(12) United States Patent
Tuten

(10) Patent No.: US 10,159,480 B2
(45) Date of Patent: Dec. 25, 2018

(54) SURGICAL JIG ASSEMBLY FOR USE IN THE MANIPULATION AND FIXATION OF BONY STRUCTURES

(71) Applicant: Robert Tuten, Richmond, VA (US)

(72) Inventor: Robert Tuten, Richmond, VA (US)

(*) Notice: Subject to any disclaimer, the term of this patent is extended or adjusted under 35 U.S.C. 154(b) by 570 days.

(21) Appl. No.: 14/803,459

(22) Filed: Jul. 20, 2015

(65) Prior Publication Data

US 2017/0020537 A1   Jan. 26, 2017

(51) Int. Cl.
| | |
|---|---|
| *A61B 17/17* | (2006.01) |
| *A61B 17/064* | (2006.01) |
| *A61B 17/68* | (2006.01) |
| *A61B 17/88* | (2006.01) |

(52) U.S. Cl.
CPC ...... *A61B 17/0642* (2013.01); *A61B 17/1775* (2016.11); *A61B 17/68* (2013.01); *A61B 17/8866* (2013.01)

(58) Field of Classification Search
CPC ............ A61B 17/1739; A61B 17/1775; A61B 17/8866; A61B 2017/1775
See application file for complete search history.

(56) References Cited

U.S. PATENT DOCUMENTS

| | | | | |
|---|---|---|---|---|
| 5,219,349 A | * | 6/1993 | Krag ................. | A61B 17/7077 606/105 |
| 6,565,568 B1 | * | 5/2003 | Rogozinski ........ | A61B 17/7055 606/102 |
| 8,740,902 B2 | * | 6/2014 | Brodsky ............ | A61B 17/1725 606/62 |

* cited by examiner

*Primary Examiner* — Anu Ramana
(74) *Attorney, Agent, or Firm* — Clements Bernard Walker PLLC; Christopher L. Bernard

(57) ABSTRACT

A surgical jig assembly that is configured to hold and manipulate a first bone segment and a second bone segment, including: a first member that is configured to be selectively coupled to the first bone segment; a second member coupled to the first member, wherein the second member selectively translates with respect to the first member along a first axis; a third member coupled to the second member, wherein the third member selectively translates with respect to the second member along a second axis, wherein the second axis is perpendicular to the first axis; and a fourth member coupled to the third member, wherein the fourth member selectively translates with respect to the third member along a third axis, wherein the third axis is perpendicular to the first axis and the second axis, and wherein the fourth member is configured to be selectively coupled to the second bone segment.

5 Claims, 24 Drawing Sheets

SURGICAL JIG ASSEMBLY FOR USE IN THE MANIPULATION AND FIXATION OF BONY STRUCTURES

FIELD OF THE INVENTION

The present invention relates generally to a surgical jig assembly for use in the manipulation and fixation of bony structures. More specifically, the present invention relates to a surgical jig assembly that may be used in calcaneal slide osteotomy procedures for the correction of hind foot deformities.

BACKGROUND OF THE INVENTION

In a calcaneal slide osteotomy procedure for the correction of a hind foot deformity, as well as in many other surgical procedures, it is desirable that a first bone segment and a second bone segment be securely held by a surgical jig assembly or the like, such that the first bone segment and the second bone segment may be translated or otherwise moved relative to one another prior to subsequent fixation being performed. In such cases, it is desirable that the surgical jig assembly provide three axes of manipulation. To date, no such adequate surgical jig assembly has been developed or produced.

BRIEF SUMMARY OF THE INVENTION

In various exemplary embodiments, the present invention provides a surgical jig assembly that may be used in a calcaneal slide osteotomy procedure for the correction of a hind foot deformity, as well as in many other surgical procedures. The surgical jig assembly is configured to securely hold a first bone segment and a second bone segment, such that the first bone segment and the second bone segment may be translated or otherwise moved relative to one another prior to subsequent fixation being performed. The surgical jig assembly provides three axes of manipulation of the osteotomy fragments or the like. In general, the surgical jig assembly includes a first member that is threadedly coupled to a second member that is primarily arranged perpendicular to the first member. The first member and the second member translate with respect to one another along a first axis. The second member is threadedly coupled to a third member that is primarily arranged perpendicular to the second member. The second member and the third member translate with respect to one another along a second axis. The third member is threadedly coupled to a fourth member that is primarily arranged coaxial with the third member. The third member and the fourth member translate with respect to one another along a third axis. The first axis, the second axis, and the third axis are all arranged perpendicular with respect to one another. Optionally, rotational motion around any of the axes may also be provided. The first member and the fourth member each include bone engagement posts or apertures that are configured to receive bone engagement pins. The surgical jig assembly is designed to apply force to these bone engagement pins, thereby causing manipulation and/or fixation of the attached bone segments via threaded adjustment of the various members and coupling connections.

In various exemplary embodiments, the present invention also provides enabling handles, drill guides, cut guides, implant devices, implant device inserters, depth gauges, and screws.

In one exemplary embodiment, the present invention provides a surgical jig assembly that is configured to hold and manipulate a first bone segment and a second bone segment, including: a first member that is configured to be selectively coupled to the first bone segment; a second member coupled to the first member, wherein the second member selectively translates with respect to the first member along a first axis; a third member coupled to the second member, wherein the third member selectively translates with respect to the second member along a second axis, wherein the second axis is perpendicular to the first axis; and a fourth member coupled to the third member, wherein the fourth member selectively translates with respect to the third member along a third axis, wherein the third axis is perpendicular to the first axis and the second axis, and wherein the fourth member is configured to be selectively coupled to the second bone segment. The coupled pairs of the first member, the second member the third member, and the fourth member are threadedly coupled. Optionally, the coupled pairs of the first member, the second member the third member, and the fourth member also selectively rotate with respect one another about the various axes. The surgical jig assembly also includes alignment guides disposed on an outer surface of any of the first member, the second member, the third member, and the fourth member. The surgical jig assembly further includes a drill guide for drilling holes in the first bone segment and the second bone segment corresponding to holes associated with the first member and the fourth member, thereby allowing the first member to be selectively coupled to the first bone segment and the fourth member to be selectively coupled to the second bone segment. The surgical jig assembly still further includes a cut guide for cutting the first bone segment and the second bone segment, wherein the cut guide comprises holes corresponding to holes associated with the first member and the fourth member, and wherein the holes are configured to receive pins, thereby coupling the cut guide to and aligning the cut guide with the first member and the fourth member.

In another exemplary embodiment, the present invention provides a surgical method, including: aligning and holding a first bone segment and a second bone segment using a surgical jig assembly, including: a first member that is configured to be selectively coupled to the first bone segment; a second member coupled to the first member, wherein the second member selectively translates with respect to the first member along a first axis; a third member coupled to the second member, wherein the third member selectively translates with respect to the second member along a second axis, wherein the second axis is perpendicular to the first axis; and a fourth member coupled to the third member, wherein the fourth member selectively translates with respect to the third member along a third axis, wherein the third axis is perpendicular to the first axis and the second axis, and wherein the fourth member is configured to be selectively coupled to the second bone segment; and securing the first bone segment and the second bone segment as aligned using an implant device. The coupled pairs of the first member, the second member the third member, and the fourth member are threadedly coupled. Optionally, the coupled pairs of the first member, the second member the third member, and the fourth member also selectively rotate with respect one another about the various axes. The surgical jig assembly also includes alignment guides disposed on an outer surface of any of the first member, the second member, the third member, and the fourth member. The surgical jig assembly further includes a drill guide for drilling holes in the first bone segment and the second bone segment corresponding to holes associated with the first member and the fourth member, thereby allowing the first member to be selectively coupled to the first bone segment and the fourth member to be selectively coupled to the second bone segment. The surgical jig assembly still further includes a cut guide for cutting the first bone segment and the second bone segment, wherein the cut guide comprises holes corresponding to holes associated with the first member and the fourth member, and wherein the holes are configured to receive pins, thereby coupling the cut guide to and aligning the cut guide with the first member and the fourth member.

In a further exemplary embodiment, the present invention provides a surgical implant device, including: a first planar portion defining a plurality of screws holes configured to selectively receive a plurality of corresponding bone screws for selectively securing the first planar portion to a bone segment; and a second portion disposed at an angle to the first planar portion, wherein the second portion comprises a plurality of friction engagement arms for selectively securing the second portion to an adjacent bone segment.

BRIEF DESCRIPTION OF THE DRAWINGS

The present invention is illustrated and described herein with reference to the various drawings, in which like reference numbers are used to denote like assembly components/method steps, as appropriate, and in which.

DETAILED DESCRIPTION OF THE INVENTION

As briefly described above, in various exemplary embodiments, the present invention provides a surgical jig assembly that may be used in a calcaneal slide osteotomy procedure for the correction of a hind foot deformity, as well as in many other surgical procedures. The surgical jig assembly is configured to securely hold a first bone segment and a second bone segment, such that the first bone segment and the second bone segment may be translated or otherwise moved relative to one another prior to subsequent fixation being performed. The surgical jig assembly provides three axes of manipulation of the osteotomy fragments or the like. In general, the surgical jig assembly includes a first member that is threadedly coupled to a second member that is primarily arranged perpendicular to the first member. The first member and the second member translate with respect to one another along a first axis. The second member is threadedly coupled to a third member that is primarily arranged perpendicular to the second member. The second member and the third member translate with respect to one another along a second axis. The third member is threadedly coupled to a fourth member that is primarily arranged coaxial with the third member. The third member and the fourth member translate with respect to one another along a third axis. The first axis, the second axis, and the third axis are all arranged perpendicular with respect to one another. Optionally, rotational motion around any of the axes may also be provided. The first member and the fourth member each include bone engagement posts or apertures that are configured to receive bone engagement pins. The surgical jig assembly is designed to apply force to these bone engagement pins, thereby causing manipulation and/or fixation of the attached bone segments via threaded adjustment of the various members and coupling connections.

In various exemplary embodiments, the present invention also provides enabling handles, drill guides, cut guides, implant devices, implant device inserters, depth gauges, and screws. It should be noted that all components of the present invention may be manufactured from any suitable surgically-compatible material using conventional techniques for making medical devices, in general.

Figure 1:
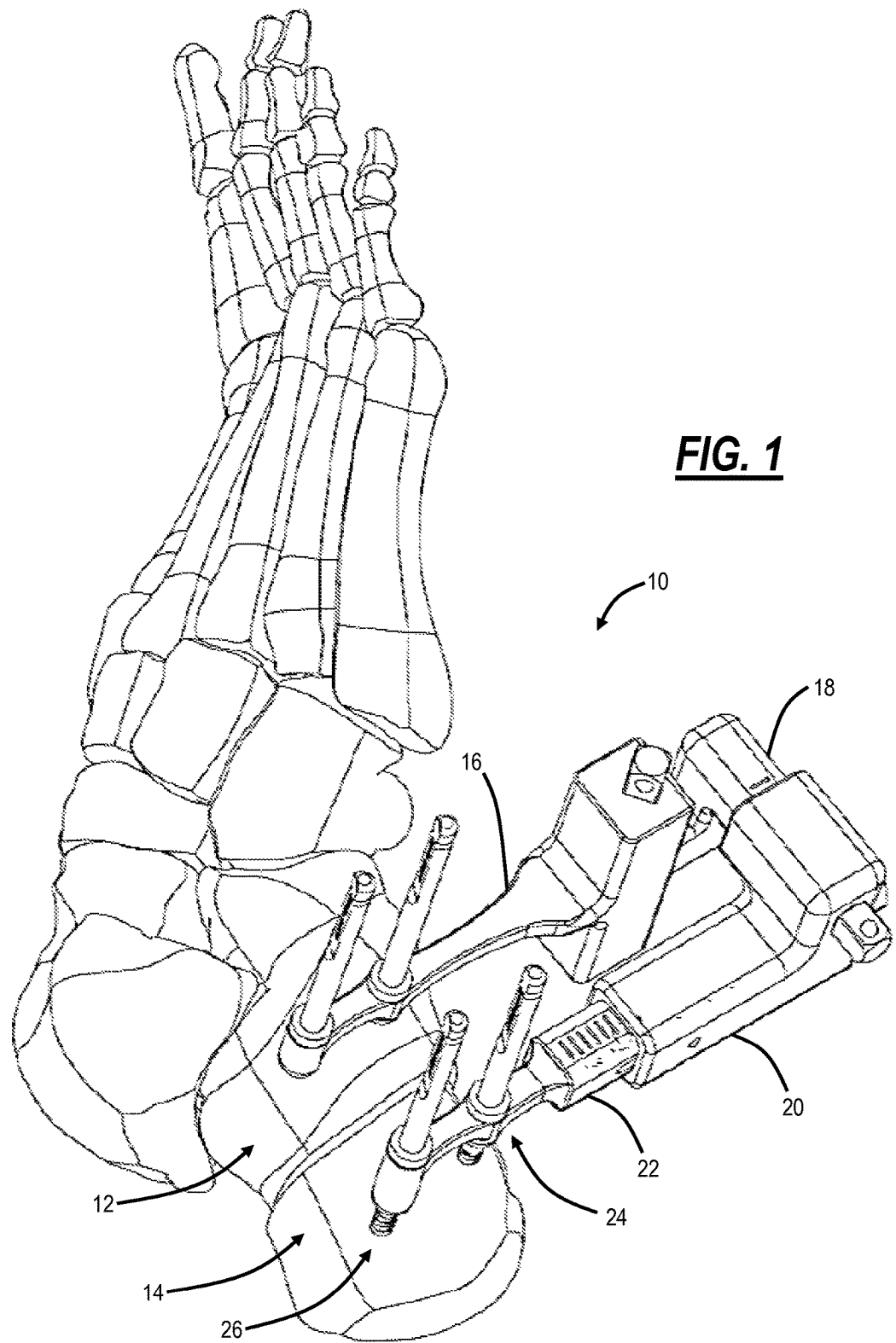
FIG. 1 is a perspective view of one exemplary embodiment of the surgical jig assembly of the present invention in use, coupled to the bony structures of the foot of a patient.

Referring now specifically to the figures, FIG. 1 is a perspective view of one exemplary embodiment of the surgical jig assembly 10 of the present invention in use, coupled to the bony structures 12 and 14 of the foot of a patient. The surgical jig assembly 10 includes a first member 16 that is threadedly coupled to a second member 18 that is primarily arranged perpendicular to the first member 16. The first member 16 and the second member 18 translate with respect to one another along a first axis. The second member 18 is threadedly coupled to a third member 20 that is primarily arranged perpendicular to the second member 18. The second member 18 and the third member 20 translate with respect to one another along a second axis. The third member 20 is threadedly coupled to a fourth member 22 that is primarily arranged coaxial with the third member 20. The third member 20 and the fourth member 22 translate with respect to one another along a third axis. The first axis, the second axis, and the third axis are all arranged perpendicular with respect to one another. Optionally, rotational motion around any of the axes may also be provided. The first member 16 and the fourth member 22 each include bone engagement posts or apertures 24 that are configured to receive bone engagement pins 26. The surgical jig assembly 10 is designed to apply force to these bone engagement pins 26, thereby causing manipulation and/or fixation of the attached bone segments 12 and 14 via threaded adjustment of the various members 16, 18, 20, and 22 and coupling connections.

Figure 2:
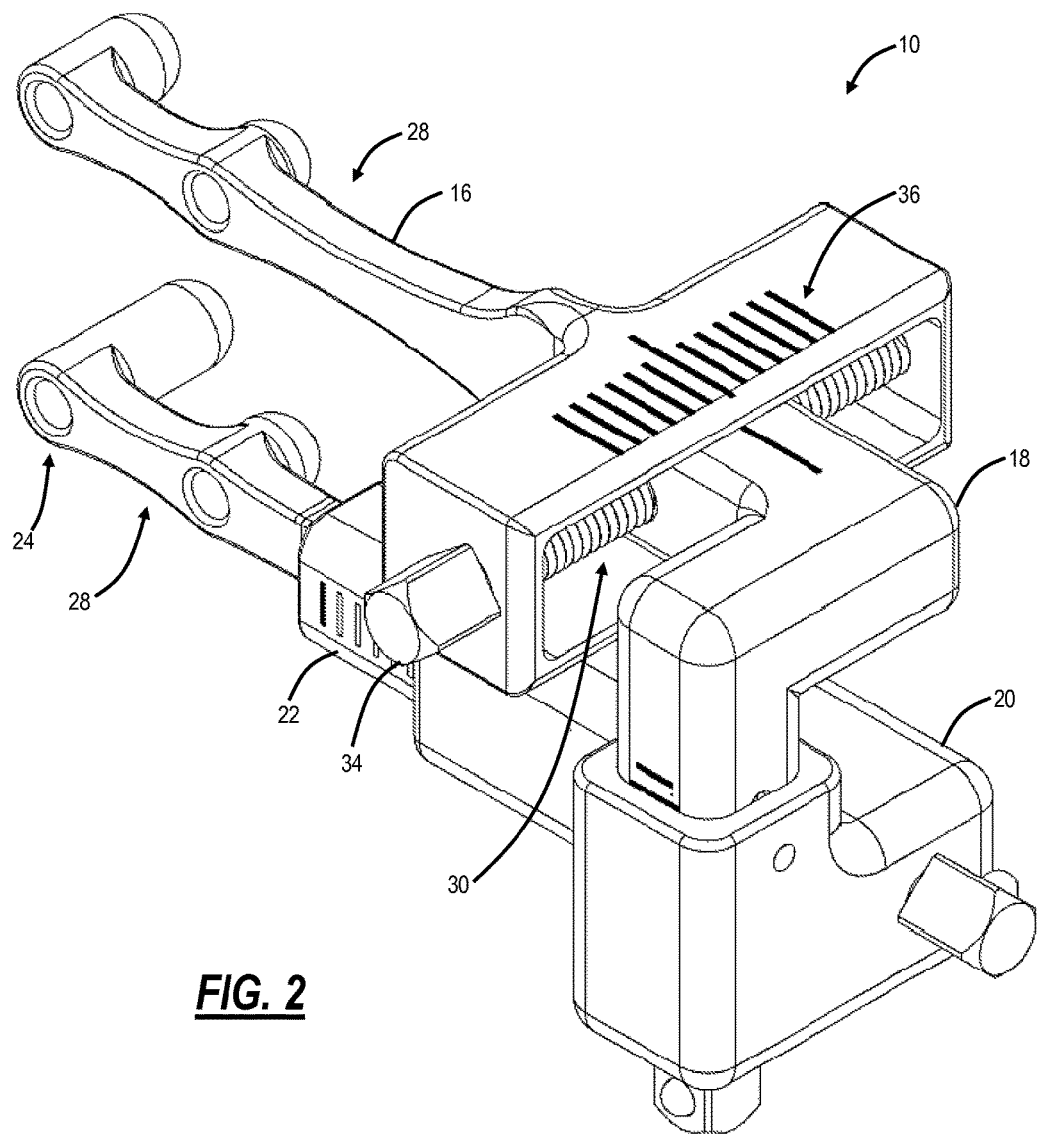
FIG. 2 is another perspective view of one exemplary embodiment of the surgical jig assembly of the present invention.

FIG. 2 is another perspective view of one exemplary embodiment of the surgical jig assembly 10 of the present invention. Preferably, the first member 16 includes an elongate bone engaging portion 28 that extends from the bulk of the surgical jig assembly 10 to the bone segment 12 (FIG. 1) engaged. This elongate bone engaging portion 28 includes the bone engagement apertures 24 through which the bone screws or pins 26 are disposed to couple the surgical jig assembly 10 to the bone segment 12. Likewise, the fourth member 22 includes an elongate bone engaging portion 28 that extends from the bulk of the surgical jig assembly 10 to the bone segment 14 (FIG. 1) engaged. This elongate bone engaging portion 28 includes the bone engagement apertures 24 through which the bone screws or pins 26 are disposed to couple the surgical jig assembly 10 to the bone segment 14. The opposite end of the first member 16 includes an internal channel 30 that is configured to receive an end of the second member 18, allowing the second member 18 to translate in an axial manner along the length of the internal channel 30. This translation is accomplished via the rotation of a screw 32 that is disposed within the internal channel 30 and through the second member 18, which is preferably internally threaded. When a surgeon rotates the head 34 of the screw 32, the rotation of the screw 32 causes the second member 18 to translate axially along its length within the internal channel 30 and with respect to the first member 16 and the first axis. A plurality of alignment guides 36 printed on or manufactured into corresponding surfaces of the first member 16 and the second member 18 are provided for the surgeon to visually quantify the degree of this translation.

Figure 3:
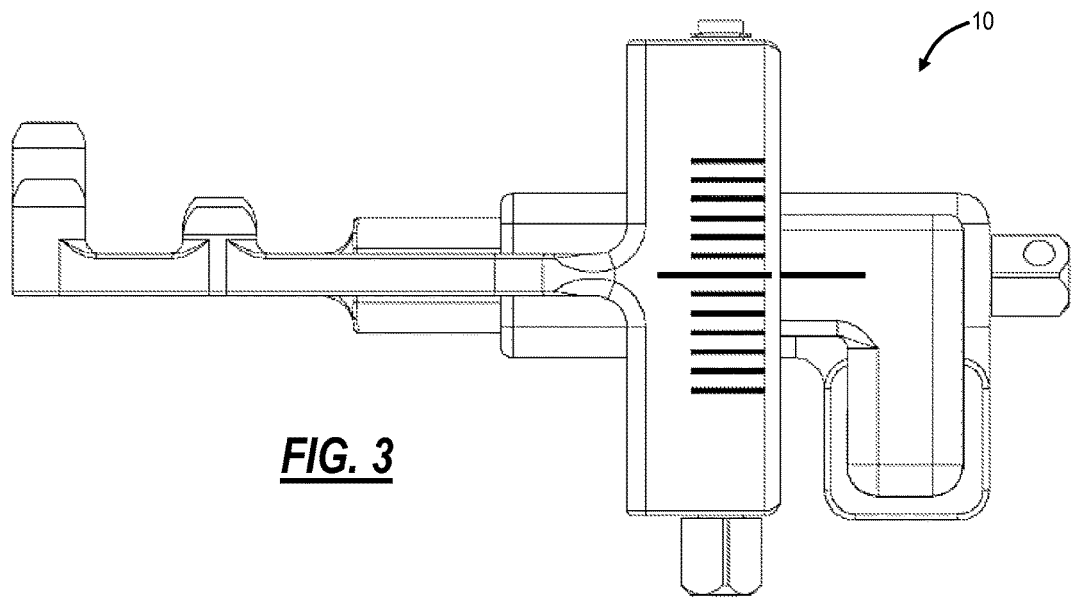
FIG. 3 is a planar view of one exemplary embodiment of the surgical jig assembly of the present invention.

FIG. 3 is a planar view further illustrating the surgical jig assembly 10 of the present invention.

Figure 4:
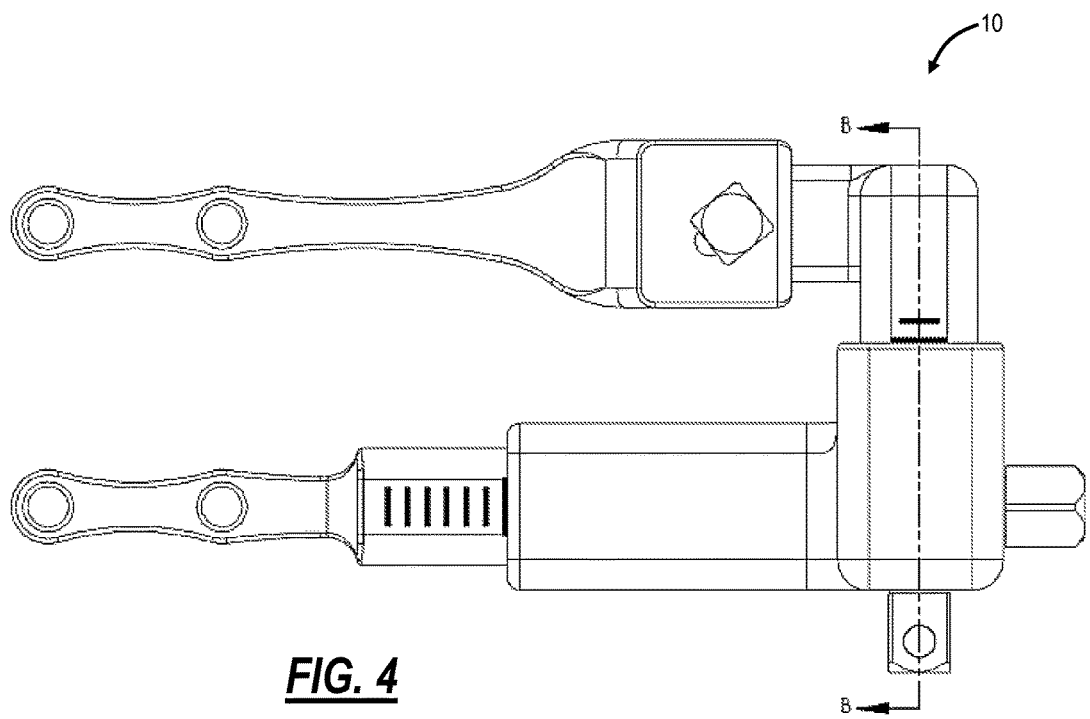
FIG. 4 is another planar view of one exemplary embodiment of the surgical jig assembly of the present invention.

FIG. 4 is another planar view further illustrating the surgical jig assembly 10 of the present invention.

Figure 5:
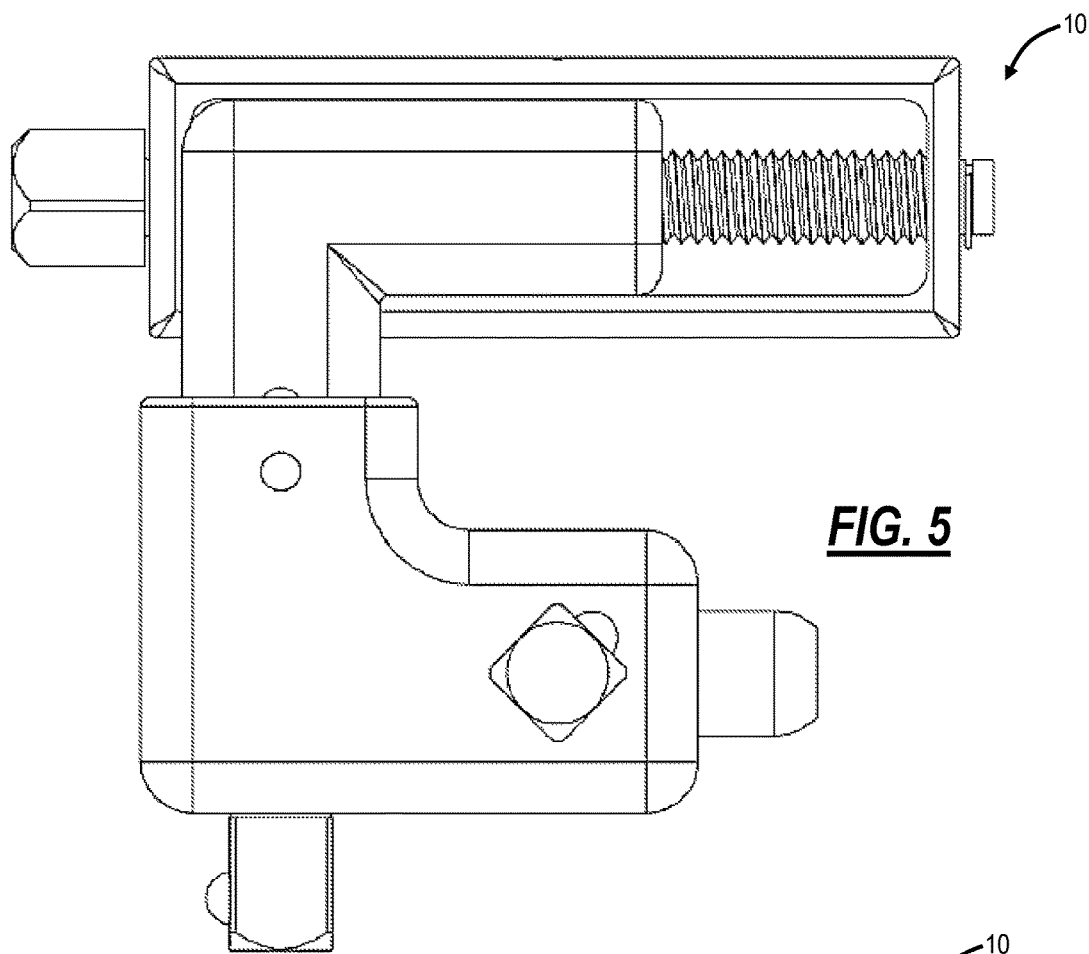
FIG. 5 is a partial planar view of one exemplary embodiment of the surgical jig assembly of the present invention.

FIG. 5 is a partial planar view further illustrating the surgical jig assembly 10 of the present invention.

Figure 6:
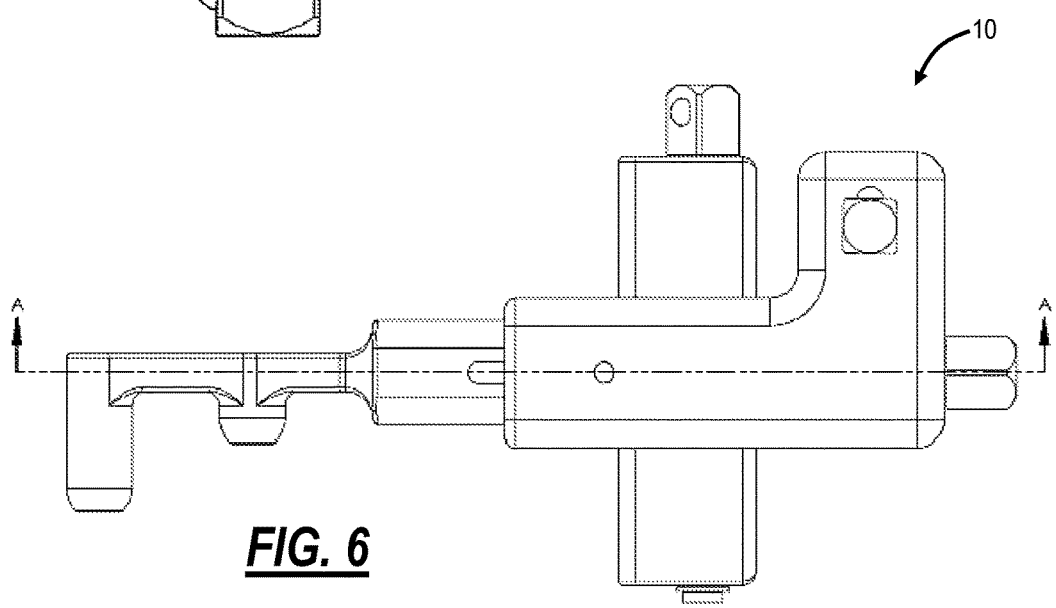
FIG. 6 is a further planar view of one exemplary embodiment of the surgical jig assembly of the present invention.

FIG. 6 is a further planar view further illustrating the surgical jig assembly 10 of the present invention.

Figure 7:
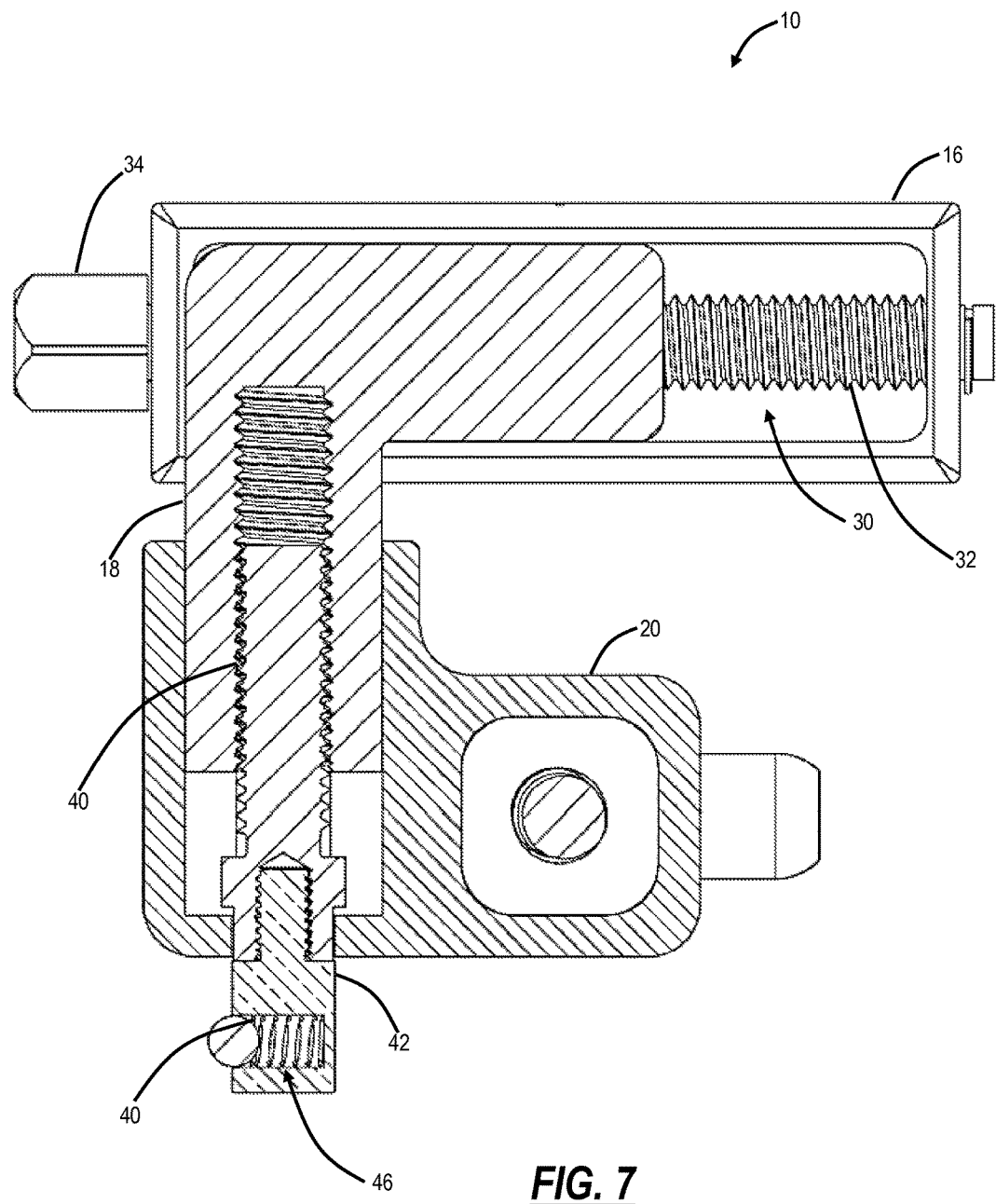
FIG. 7 is a partial cross-sectional view of one exemplary embodiment of the surgical jig assembly of the present invention.

FIG. 7 is a partial cross-sectional view of one exemplary embodiment of the surgical jig assembly of the present invention. Again, the first member 16 includes an internal channel 30 that is configured to receive an end of the second member 18, allowing the second member 18 to translate in an axial manner along the length of the internal channel 30. This translation is accomplished via the rotation of a screw 32 that is disposed within the internal channel 30 and through the second member 18, which is preferably internally threaded. When a surgeon rotates the head 34 of the screw 32, the rotation of the screw 32 causes the second member 18 to translate axially along its length within the internal channel 30 and with respect to the first member 16 and the first axis. Likewise, the third member 20 includes an internal channel 38 that is configured to receive an opposite end of the second member 18, allowing the second member 18 to translate in an axial manner along the length of the internal channel 38. This translation is accomplished via the rotation of another screw 40 that is disposed within the internal channel 38 and through the second member 18, which is preferably internally threaded. When a surgeon rotates the head 42 of the screw 40, the rotation of the screw 40 causes the second member 18 to translate axially along its length within the internal channel 38 and with respect to the third member 20 and the second axis, which is perpendicular to the first axis. As may be seen in FIG. 7, the head 42 of the screw 40 (and the heads of all screws of the present invention) may include some sort of retention mechanism that allows an actuation handle or other tool to be affixed to the head 42 for actuation and then removed. In this particular embodiment, the retention mechanism includes a depressible bearing 44 biased by a spring 46, the depressible bearing 44 selectively mating with a corresponding recess associated with the actuation handle or other tool, although any suitable retention mechanism may be utilized.

Figure 8:
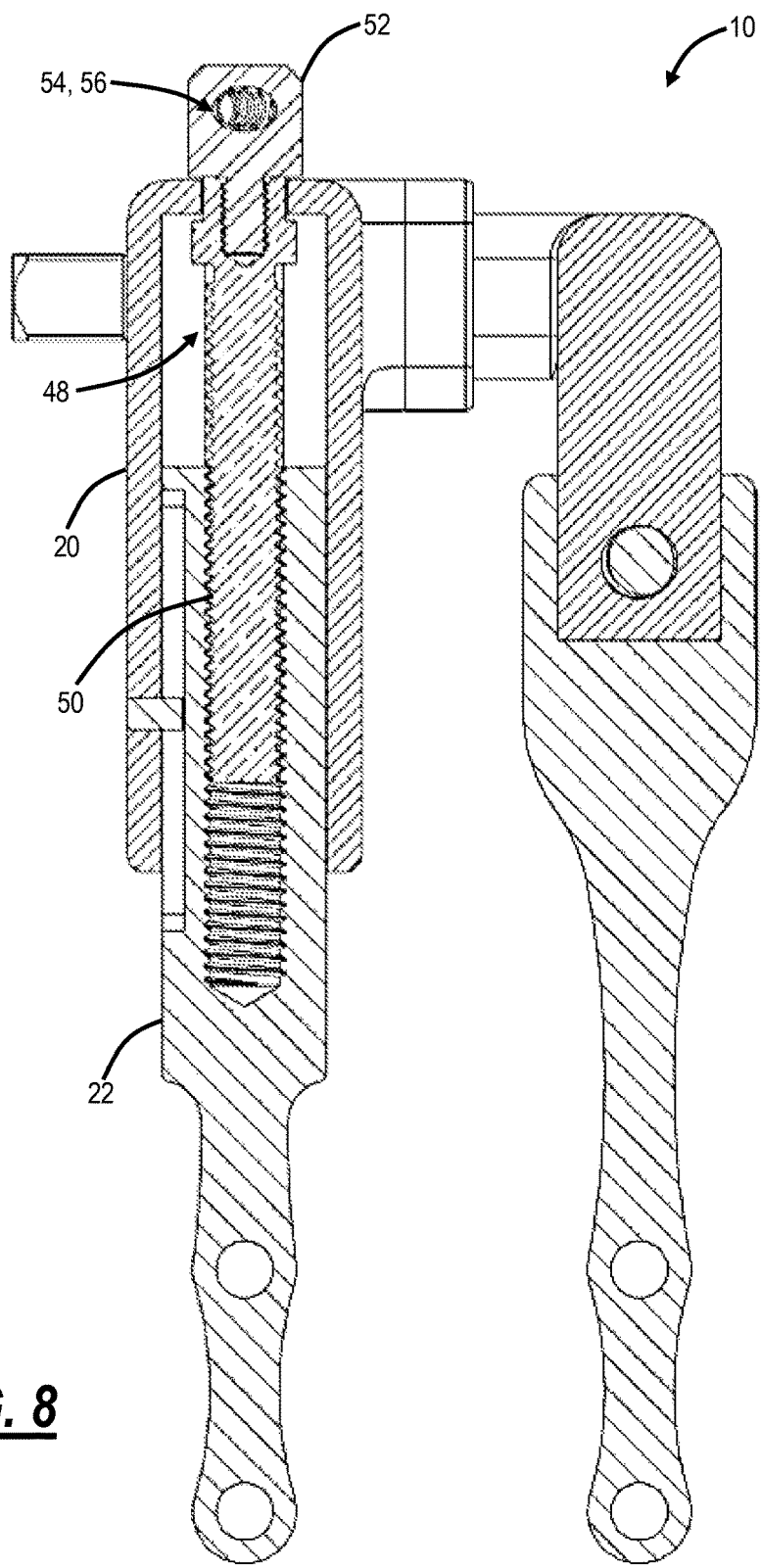
FIG. 8 is a cross-sectional view of one exemplary embodiment of the surgical jig assembly of the present invention.

FIG. 8 is a cross-sectional view of one exemplary embodiment of the surgical jig assembly of the present invention. The opposite end of the third member 20 also includes an internal channel 48 that is configured to receive an end of the fourth member 22, allowing the fourth member to translate in an axial manner along the length of the internal channel 48. This translation is accomplished via the rotation of another screw 50 that is disposed within the internal channel 48 and through the fourth member 22, which is preferably internally threaded. When a surgeon rotates the head 52 of the screw 50, the rotation of the screw 50 causes the fourth member 22 to translate axially along its length within the internal channel 48 and coaxially with respect to the third member 20 and the third axis, which is perpendicular to the first axis and the second axis. As may be seen in FIG. 8, the head 52 of the screw 50 (and the heads of all screws of the present invention) may include some sort of retention mechanism that allows an actuation handle or other tool to be affixed to the head 52 for actuation and then removed. In this particular embodiment, the retention mechanism includes a depressible bearing 54 biased by a spring 56, the depressible bearing 54 selectively mating with a corresponding recess associated with the actuation handle or other tool, although any suitable retention mechanism may be utilized.

Figure 9:
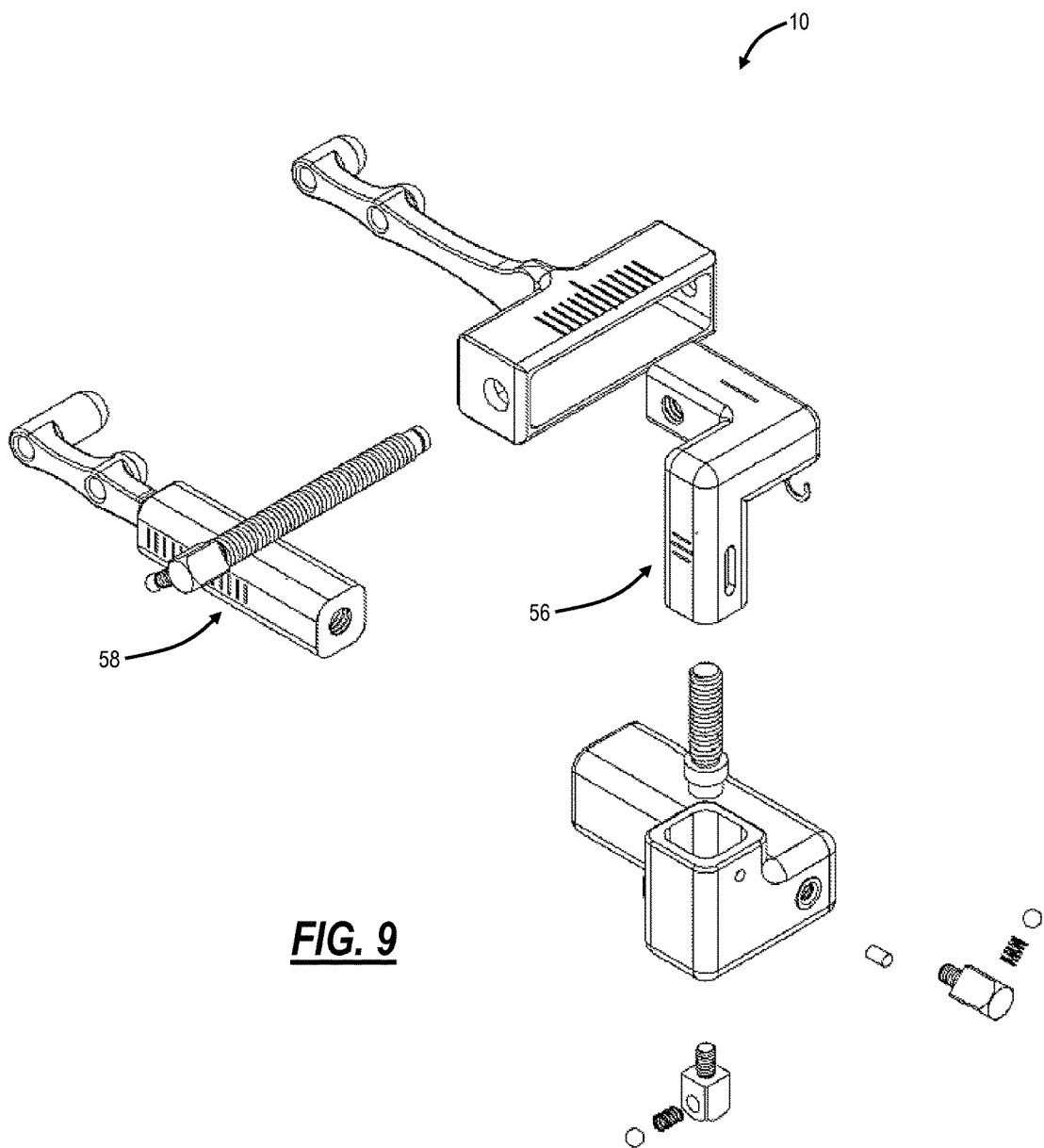
FIG. 9 is an exploded perspective view of one exemplary embodiment of the surgical jig assembly of the present invention.

FIG. 9 is an exploded perspective view of one exemplary embodiment of the surgical jig assembly of the present invention. Again, a plurality of alignment guides 56 printed on or manufactured into corresponding surfaces of the second member 18 and the third member 20 are provided for the surgeon to visually quantify the degree of translation. Further, a plurality of alignment guides 58 printed on or manufactured into corresponding surfaces of the third member 20 and the fourth member 22 are provided for the surgeon to visually quantify the degree of translation.

Figure 10:
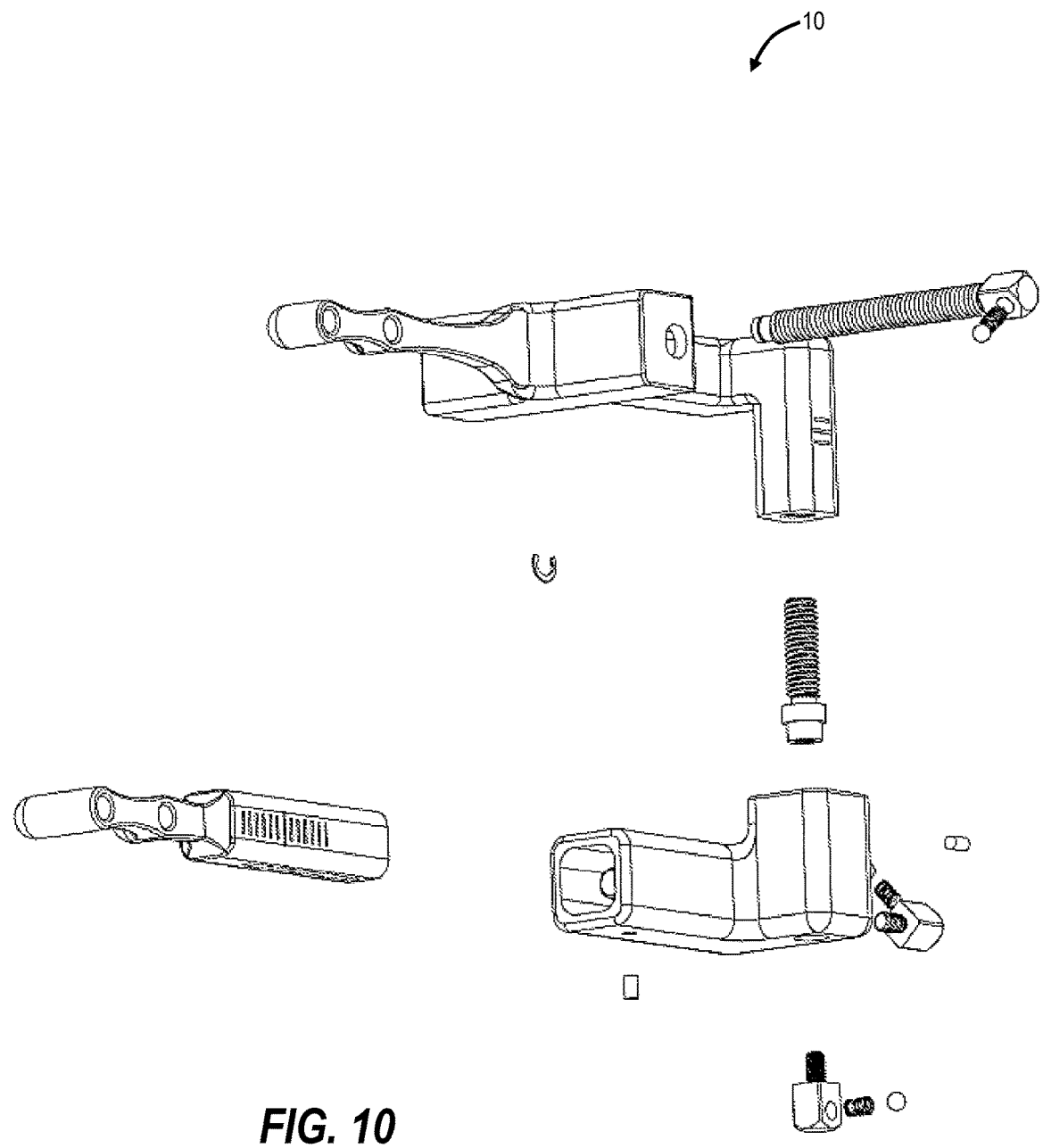
FIG. 10 is another exploded perspective view of one exemplary embodiment of the surgical jig assembly of the present invention.

FIG. 10 is another exploded perspective view further illustrating the surgical jig assembly 10 of the present invention.

Figure 11:
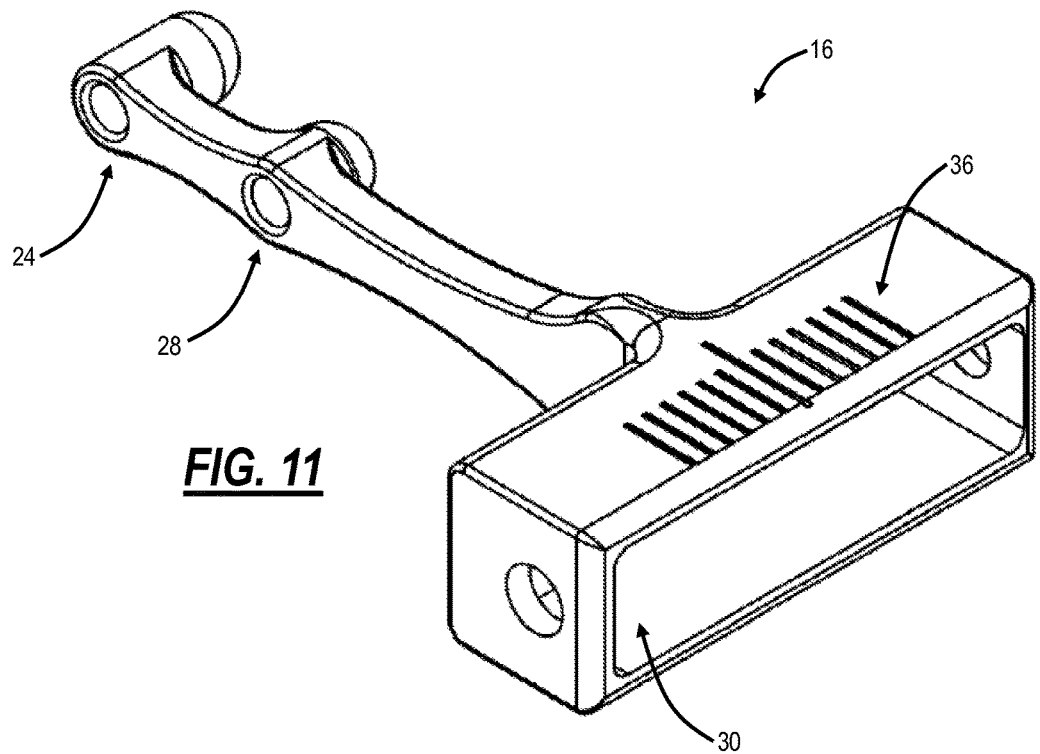
FIG. 11 is a partial perspective view of one exemplary embodiment of the surgical jig assembly of the present invention.

FIG. 11 is a partial perspective view of one exemplary embodiment of the surgical jig assembly 10 (FIGS. 1-10) of the present invention. Again, the first member 16 includes an elongate bone engaging portion 28 that extends from the bulk of the surgical jig assembly 10 to the bone segment 12 (FIG. 1) engaged. This elongate bone engaging portion 28 includes the bone engagement apertures 24 through which the bone screws or pins 26 (FIG. 1) are disposed to couple the surgical jig assembly 10 to the bone segment 12. The opposite end of the first member 16 includes an internal channel 30 that is configured to receive an end of the second member 18 (FIGS. 1-10), allowing the second member 18 to translate in an axial manner along the length of the internal channel 30. This translation is accomplished via the rotation of a screw 32 (FIGS. 2, 5, 7, 9, and 10) that is disposed within the internal channel 30 and through the second member 18, which is preferably internally threaded. When a surgeon rotates the head 34 (FIGS. 1-10) of the screw 32, the rotation of the screw 32 causes the second member 18 to translate axially along its length within the internal channel 30 and with respect to the first member 16 and the first axis. A plurality of alignment guides 36 printed on or manufactured into corresponding surfaces of the first member 16 and the second member 18 are provided for the surgeon to visually quantify the degree of this translation.

Figure 12:
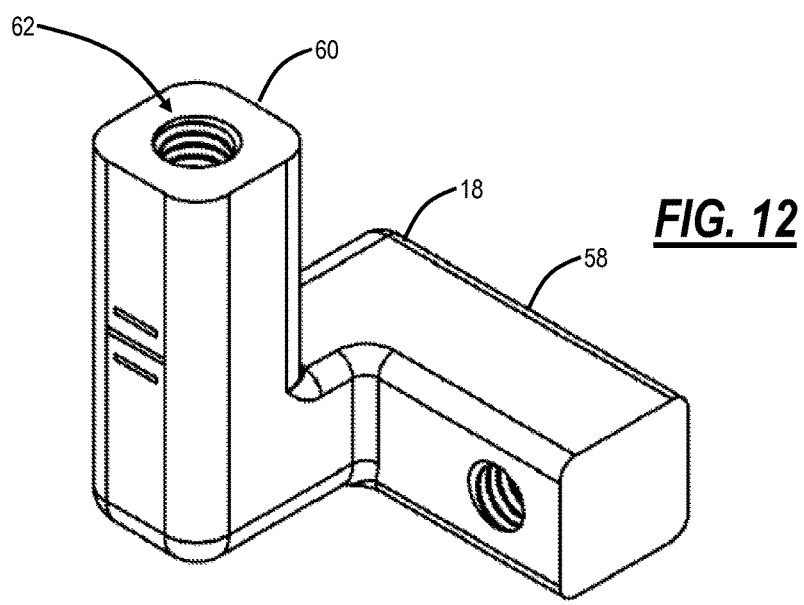
FIG. 12 is another partial perspective view of one exemplary embodiment of the surgical jig assembly of the present invention.

FIG. 12 is another partial perspective view of one exemplary embodiment of the surgical jig assembly 10 (FIGS. 1-10) of the present invention, highlighting the fact that the second member 18 may include a first arm or portion 58 and a second arm or portion 60, each configured to couple with a different member (i.e. first 16 or third 20) via an internally threaded screw hole 62 configured to receive the corresponding screw 32 or 40. In this exemplary embodiment, the first arm portion 58 and the second arm portion 60 are aligned substantially-perpendicularly to one another and represent a "double-L" configuration, although other suitable configurations may be utilized.

Figure 13:
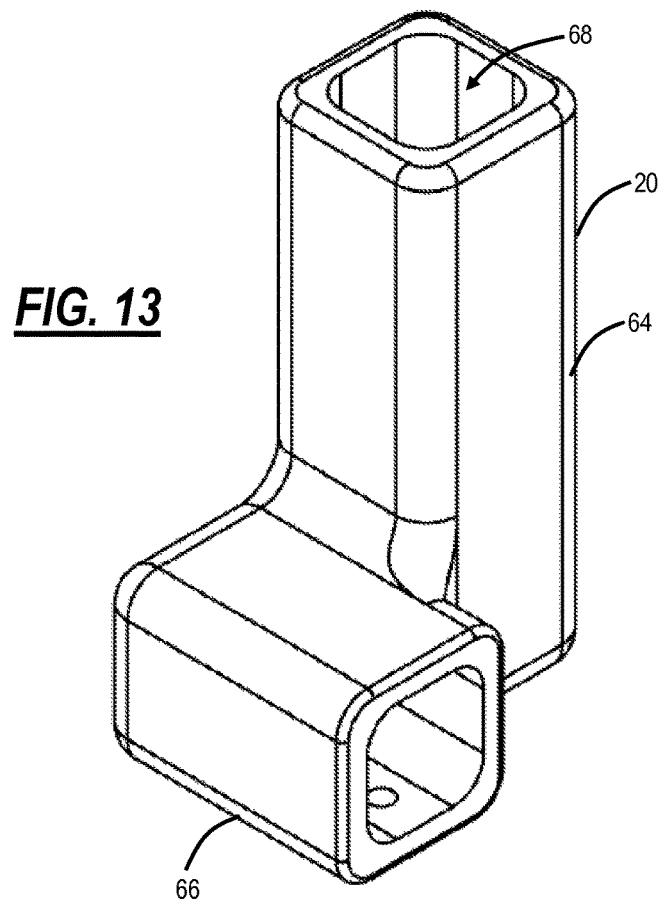
FIG. 13 is a further partial perspective view of one exemplary embodiment of the surgical jig assembly of the present invention.

FIG. 13 is a further partial perspective view of one exemplary embodiment of the surgical jig assembly 10 (FIGS. 1-10) of the present invention, highlighting the fact that the third member 20 may include a first arm or portion 64 and a second arm or portion 66, each configured to couple with a different member (i.e. second 18 or fourth 22) via an internal aperture 68 configured to receive the corresponding member 18 or 22. In this exemplary embodiment, the first arm portion 64 and the second arm portion 66 are aligned substantially-perpendicularly to one another and represent a "double-L" configuration, although other suitable configurations may be utilized.

Figure 14:
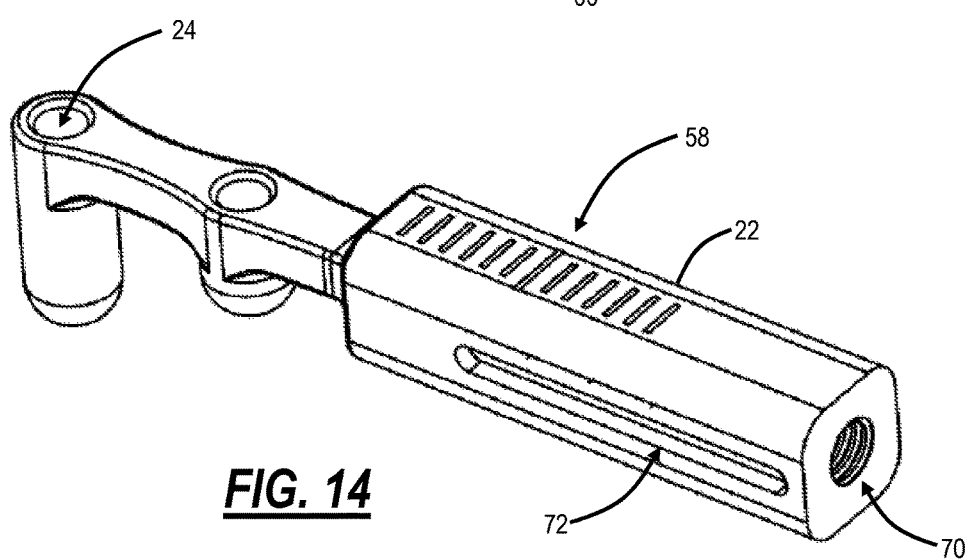
FIG. 14 is a still further partial perspective view of one exemplary embodiment of the surgical jig assembly of the present invention.

FIG. 14 is a still further partial perspective view of one exemplary embodiment of the surgical jig assembly 10 (FIGS. 1-10) of the present invention. Again, the fourth member 22 includes an elongate bone engaging portion 28 that extends from the bulk of the surgical jig assembly 10 to the bone segment 14 (FIG. 1) engaged. This elongate bone engaging portion 28 includes the bone engagement apertures 24 through which the bone screws or pins 26 (FIG. 1) are disposed to couple the surgical jig assembly 10 to the bone segment 14. The opposite end of the fourth member 22 includes an internally threaded screw hole 70 for receiving the screw 50 (FIGS. 8, 9, and 10) associated with the third member 20 (FIGS. 1-10 and 13). Again, a plurality of alignment guides 58 printed on or manufactured into corresponding surfaces of the third member 20 and the fourth member 22 are provided for the surgeon to visually quantify the degree of translation. Finally, the fourth member 22 (and optionally all other members 16, 18, and 20) include either a slot 72 or corresponding through hole configured to receive a pin that acts as a stop to prevent over-translation in either direction of one member with respect to another.

Figure 15:
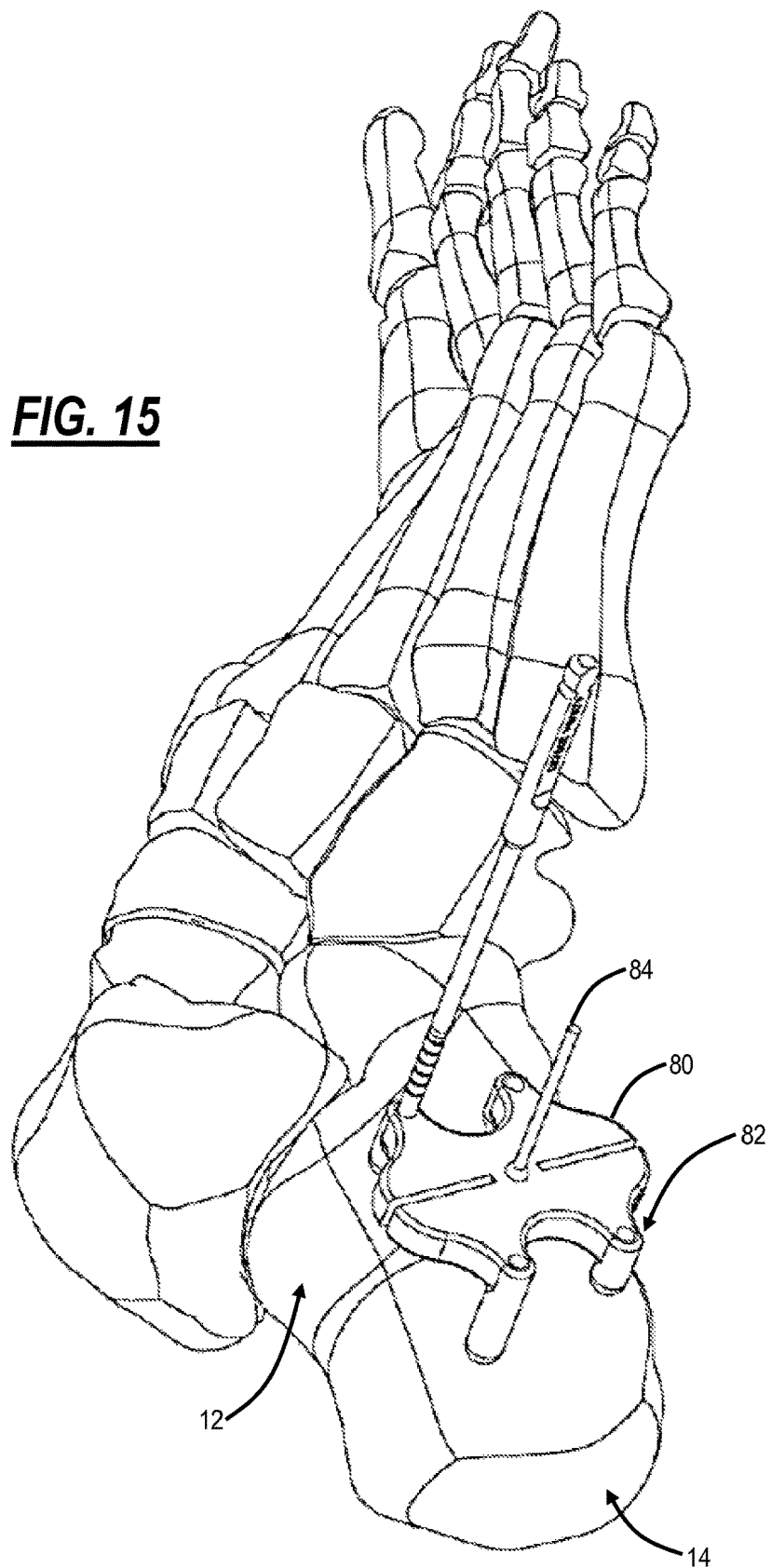
FIG. 15 is a perspective view of one exemplary embodiment of the surgical jig assembly drill guide of the present invention in use, coupled to the bony structures of the foot of a patient.

FIG. 15 is a perspective view of one exemplary embodiment of the surgical jig assembly drill guide 80 of the present invention in use, coupled to the bony structures 12 and 14 of the foot of a patient. The drill guide 80 includes a plurality of apertures 82 through which holes are drilled for the subsequent securement of the surgical jig assembly 10 (FIGS. 1-10) of the present invention. Optionally, the drill guide 80 includes a central pin or screw 84 for initially securing the drill guide 80 to the bony structures 12 and 14 prior to the holes being drilled, thereby ensuring proper alignment of the holes with respect to one another.

Figure 16:
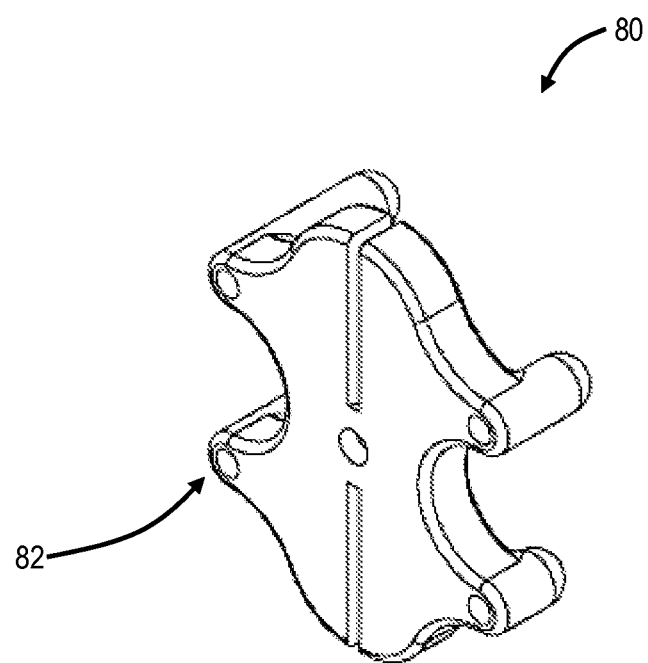
FIG. 16 is another perspective view of one exemplary embodiment of the surgical jig assembly drill guide of the present invention.

FIG. 16 is another perspective view further illustrating the surgical jig assembly drill guide 80 of the present invention.

Figure 17:
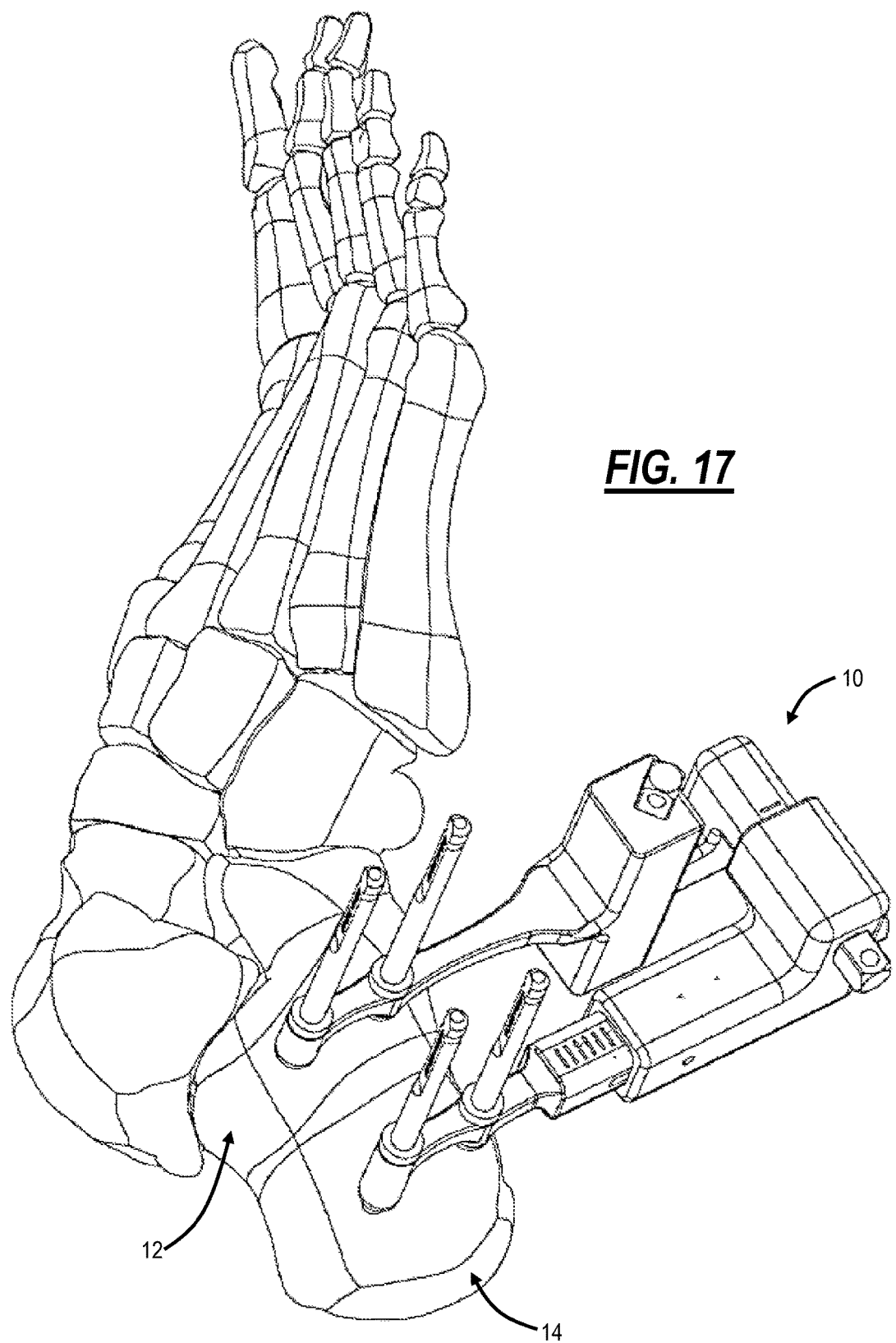
FIG. 17 is a further perspective view of one exemplary embodiment of the surgical jig assembly of the present invention in use, coupled to the bony structures of the foot of a patient.

FIG. 17 is a further perspective view further illustrating the surgical jig assembly 10 of the present invention in use, coupled to the bony structures 12 and 14 of the foot of a patient.

Figure 18:
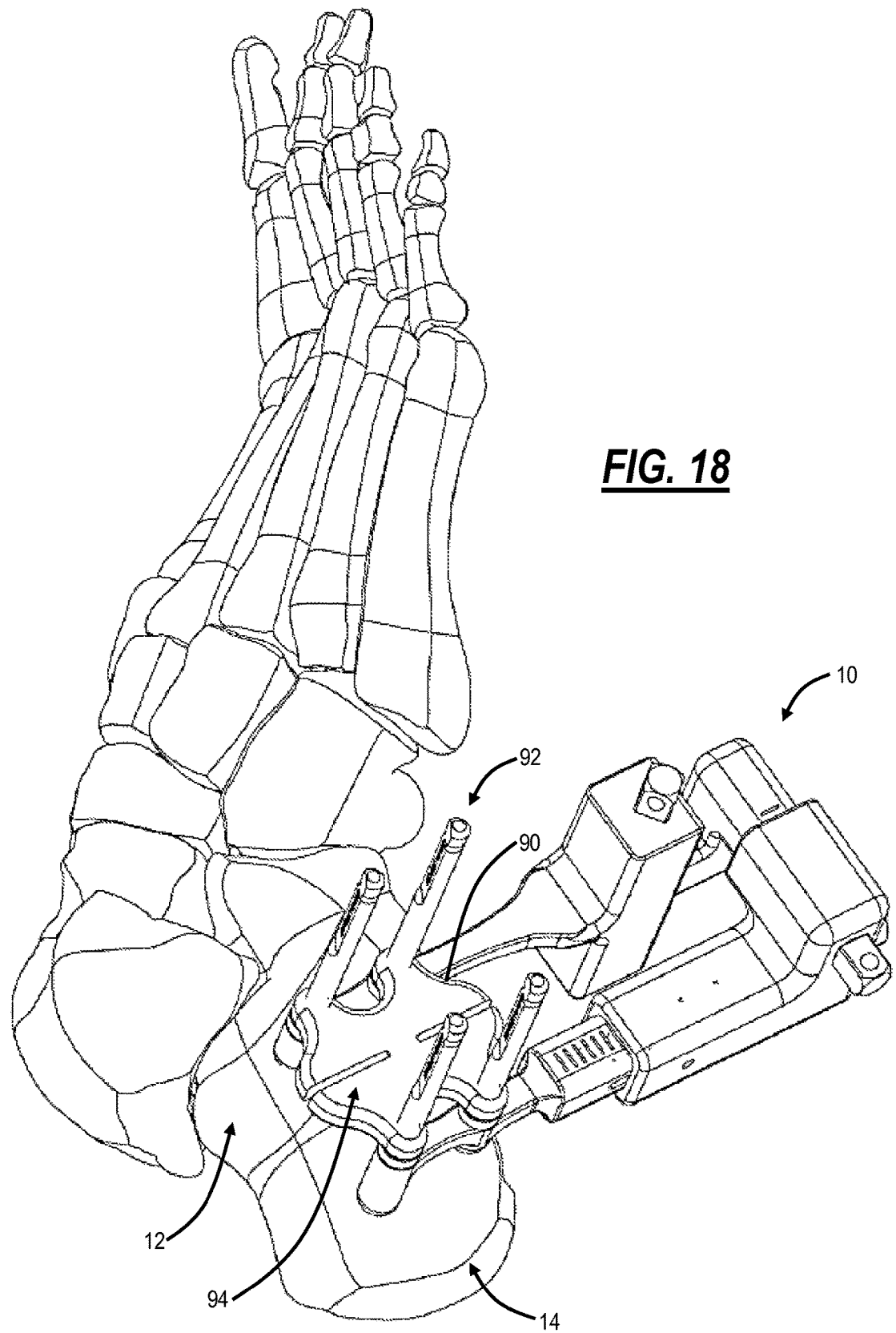
FIG. 18 is a perspective view of one exemplary embodiment of the surgical jig assembly cut guide of the present invention in use, coupled to the bony structures of the foot of a patient.

FIG. 18 is a perspective view of one exemplary embodiment of the surgical jig assembly cut guide 90 (which may optionally be the same as the drill guide 80 (FIGS. 15 and 16)) of the present invention in use, coupled to the bony structures 12 and 14 of the foot of a patient. The cut guide 90 is disposed over pins 92 inserted into the holes drilled into the bony structures 12 and 14 after the surgical jig assembly 10 is installed. The cut guide 90 includes one or more slots 94 disposed in predetermined locations through which the bony structures 12 and 14 are selectively cut, thereby providing movable bone segments 12 and 14 for alignment.

Figure 19:
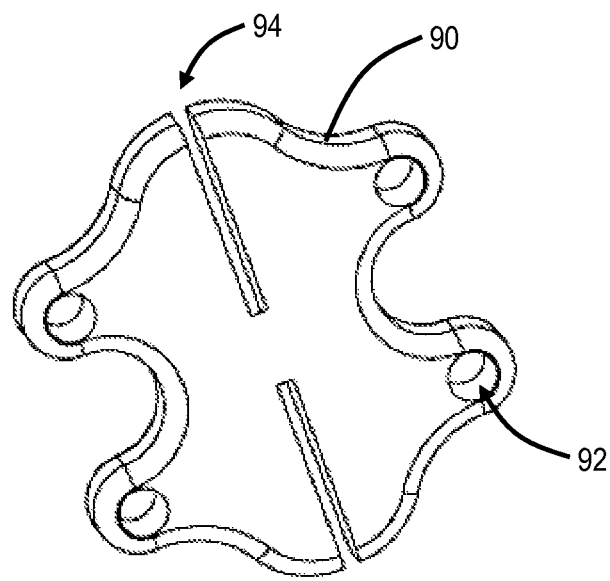
FIG. 19 is another perspective view of one exemplary embodiment of the surgical jig assembly cut guide of the present invention.

FIG. 19 is another perspective view further illustrating the surgical jig assembly cut guide 90 of the present invention.

Figure 20:
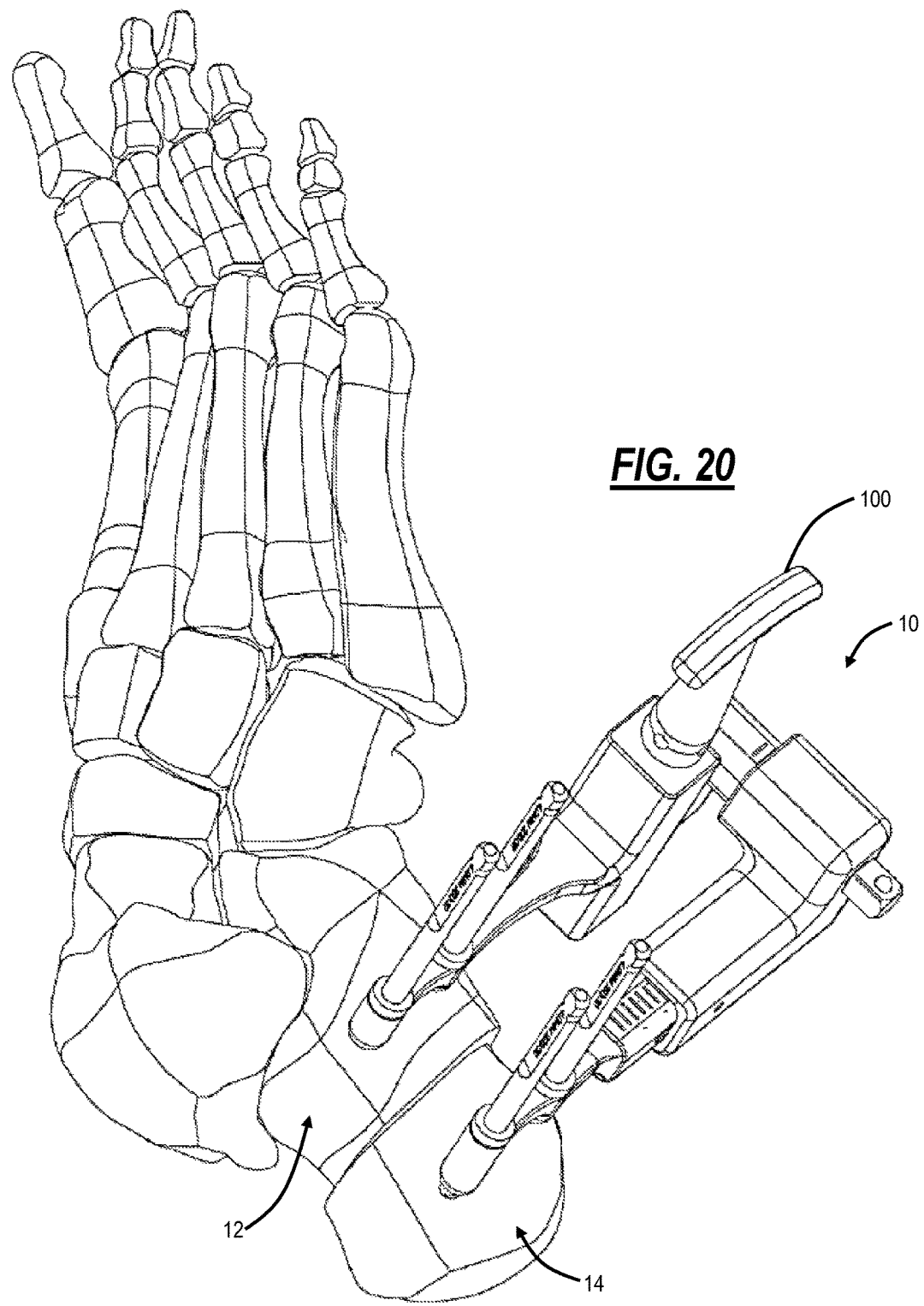
FIG. 20 is a still further perspective view of one exemplary embodiment of the surgical jig assembly of the present invention in use, coupled to the bony structures of the foot of a patient.

FIG. 20 is a still further perspective view further illustrating the surgical jig assembly 10 of the present invention in use, coupled to the bony structures 12 and 14 of the foot of a patient. In this case, an actuation handle 100 is installed on the surgical jig assembly 10 for holding and actuating the surgical jig assembly 10.

Figure 21:
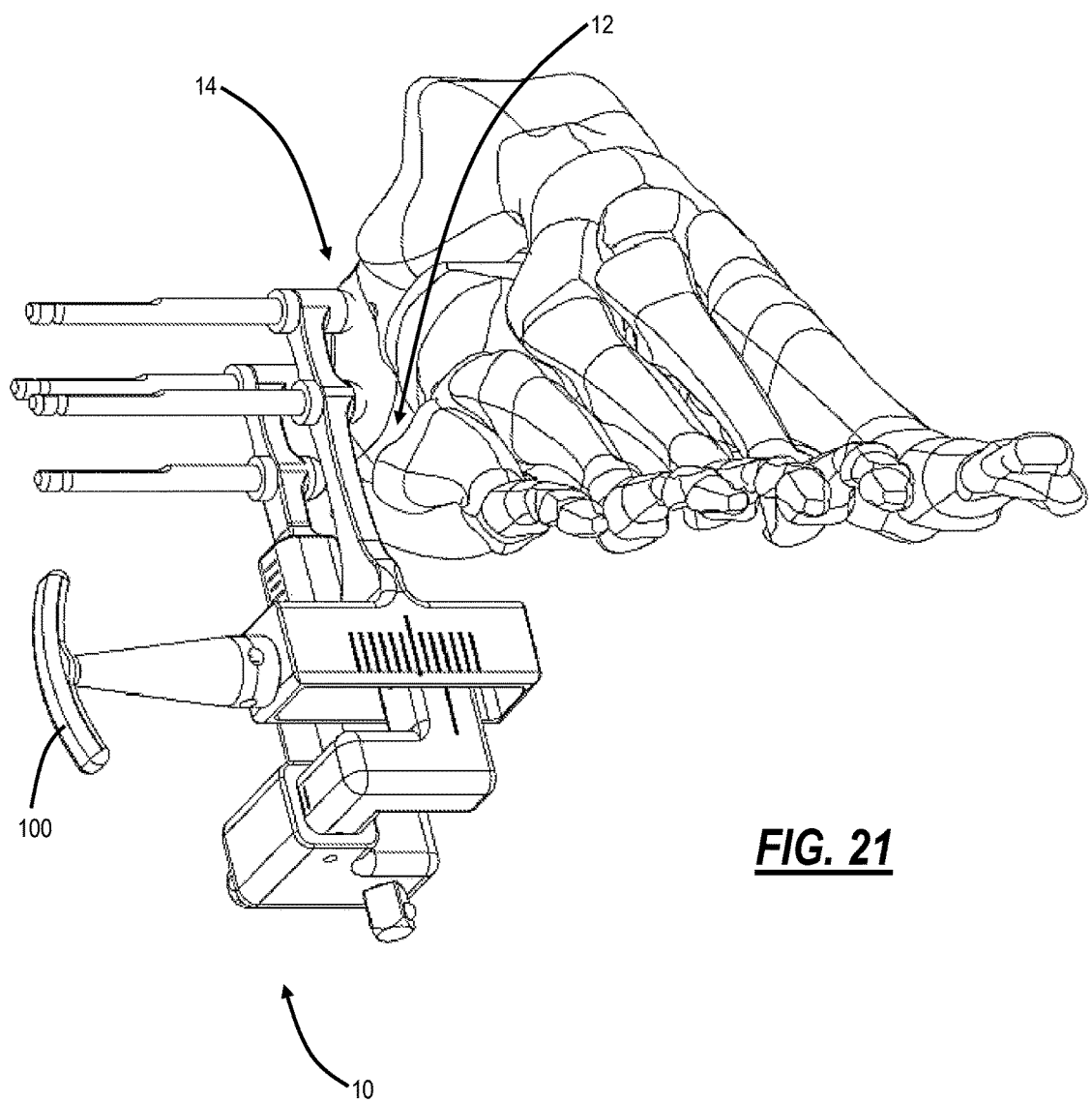
FIG. 21 is a still further perspective view of one exemplary embodiment of the surgical jig assembly of the present invention in use, coupled to the bony structures of the foot of a patient.

FIG. 21 is a still further perspective view further illustrating the surgical jig assembly 10 of the present invention in use, coupled to the bony structures 12 and 14 of the foot of a patient. In this case, an actuation handle 100 is installed on the surgical jig assembly 10 for holding and actuating the surgical jig assembly 10.

Figure 22:
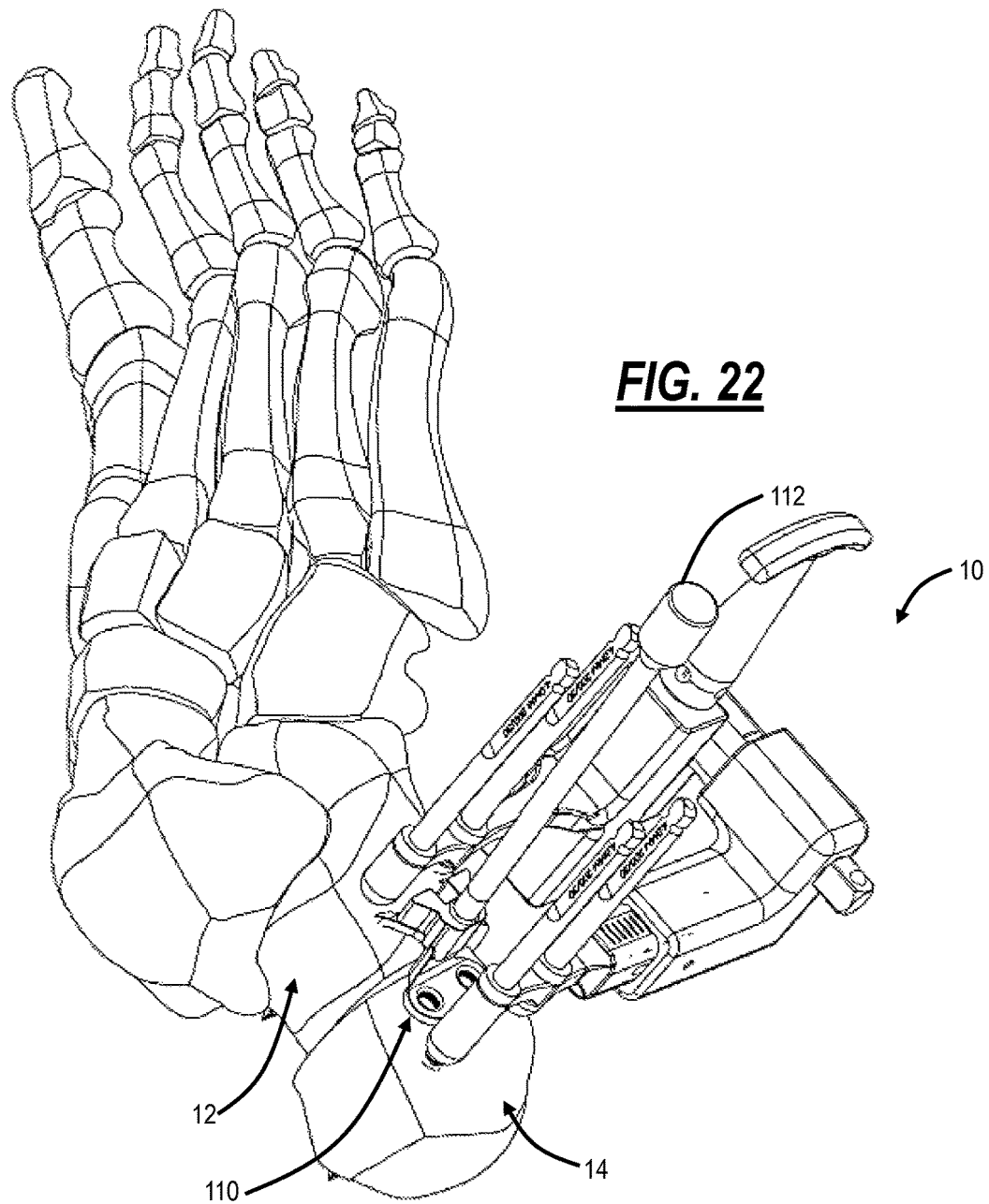
FIG. 22 is a perspective view of one exemplary embodiment of the surgical jig assembly implant device and implant device inserter of the present invention in use, coupled to the bony structures of the foot of a patient.

FIG. 22 is a perspective view of one exemplary embodiment of the surgical jig assembly implant device 110 and implant device inserter 112 of the present invention in use, coupled to the bony structures 12 and 14 of the foot of a patient.

Figure 23:
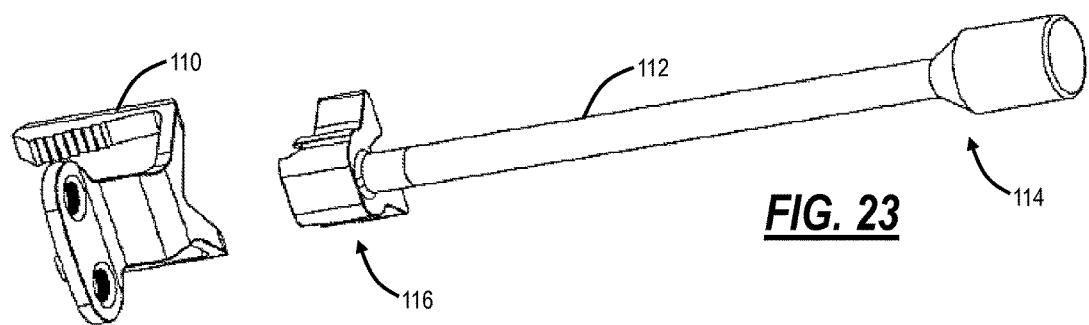
FIG. 23 is another perspective view of one exemplary embodiment of the surgical jig assembly implant device and implant device inserter of the present invention.

FIG. 23 is another perspective view of one exemplary embodiment of the surgical jig assembly implant device 110 and implant device inserter 112 of the present invention. As may be appreciated from this figure, the device inserter 112 includes a handle portion 114 and an end portion 116 that is angled and slotted such that it may be used to retain and position the implant device 110, which is correspondingly angled and slotted, while it is positioned, drilled, and secured.

Figure 24:
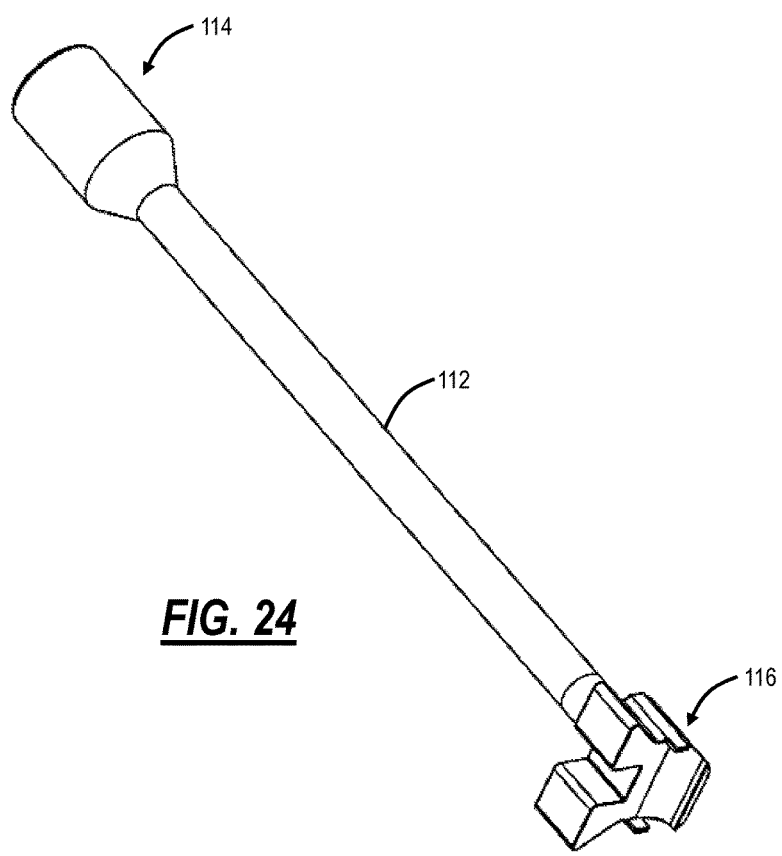
FIG. 24 is a further perspective view of one exemplary embodiment of the surgical jig assembly implant device inserter of the present invention.

FIG. 24 is a further perspective view further illustrating the surgical jig assembly implant device inserter 112 of the present invention.

Figure 25:
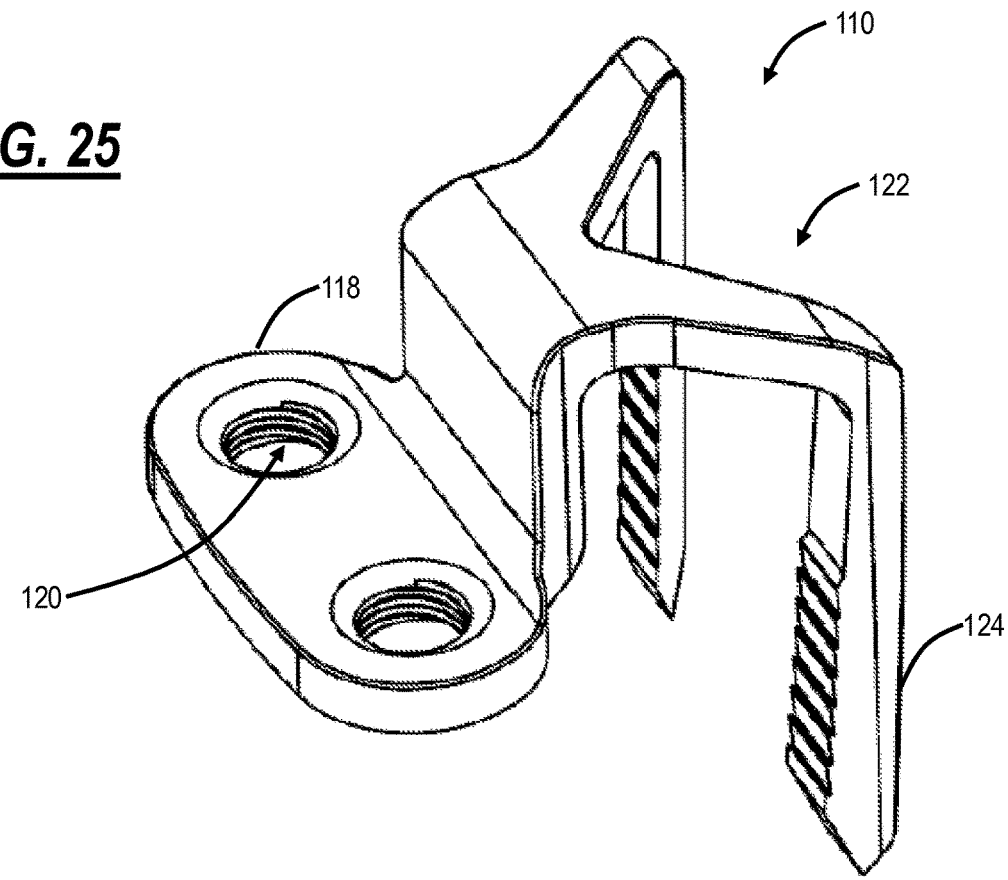
FIG. 25 is a further perspective view of one exemplary embodiment of the surgical jig assembly implant device of the present invention.

FIG. 25 is a further perspective view of one exemplary embodiment of the surgical jig assembly implant device 110 of the present invention. The implant device includes a first portion 118 incorporating a plurality of screws holes 120 for receiving a plurality of corresponding screws for securing the first portion 118 to the second bone segment 14, for example, and a second portion 122 incorporating a plurality of friction engagement arms 124 or the like for securing the second portion 122 to the first bone segment 12, for example. In this manner, the implant device 110 is used to hold the bone segments 12 and 14 in a predetermined alignment after that alignment has been established using the surgical jig assembly 10 of the present invention.

Figure 26:
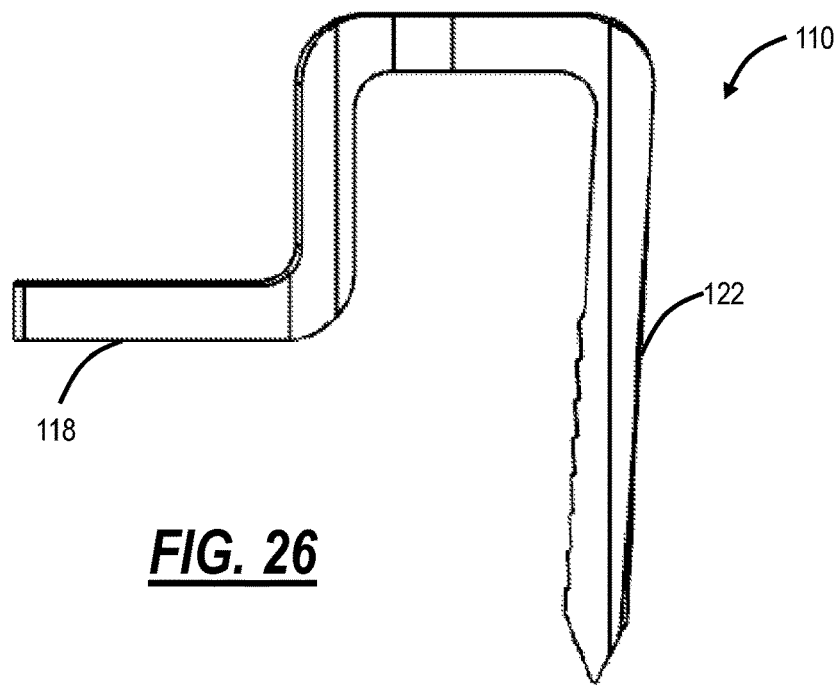
FIG. 26 is a planar view of one exemplary embodiment of the surgical jig assembly implant device of the present invention.

FIG. 26 is a planar view further illustrating the surgical jig assembly implant device 110 of the present invention.

Figure 27:
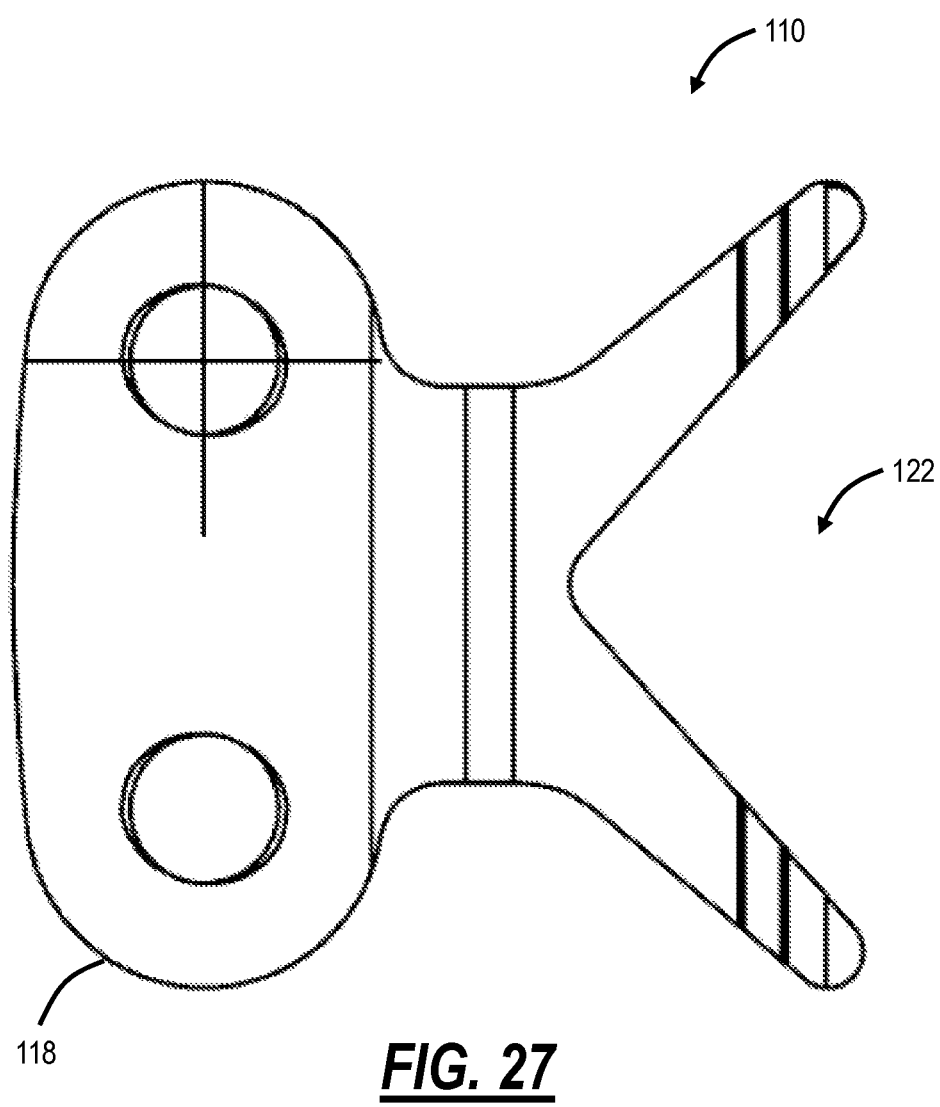
FIG. 27 is another planar view of one exemplary embodiment of the surgical jig assembly implant device of the present invention.

FIG. 27 is another planar view further illustrating the surgical jig assembly implant device 110 of the present invention.

Figure 28:
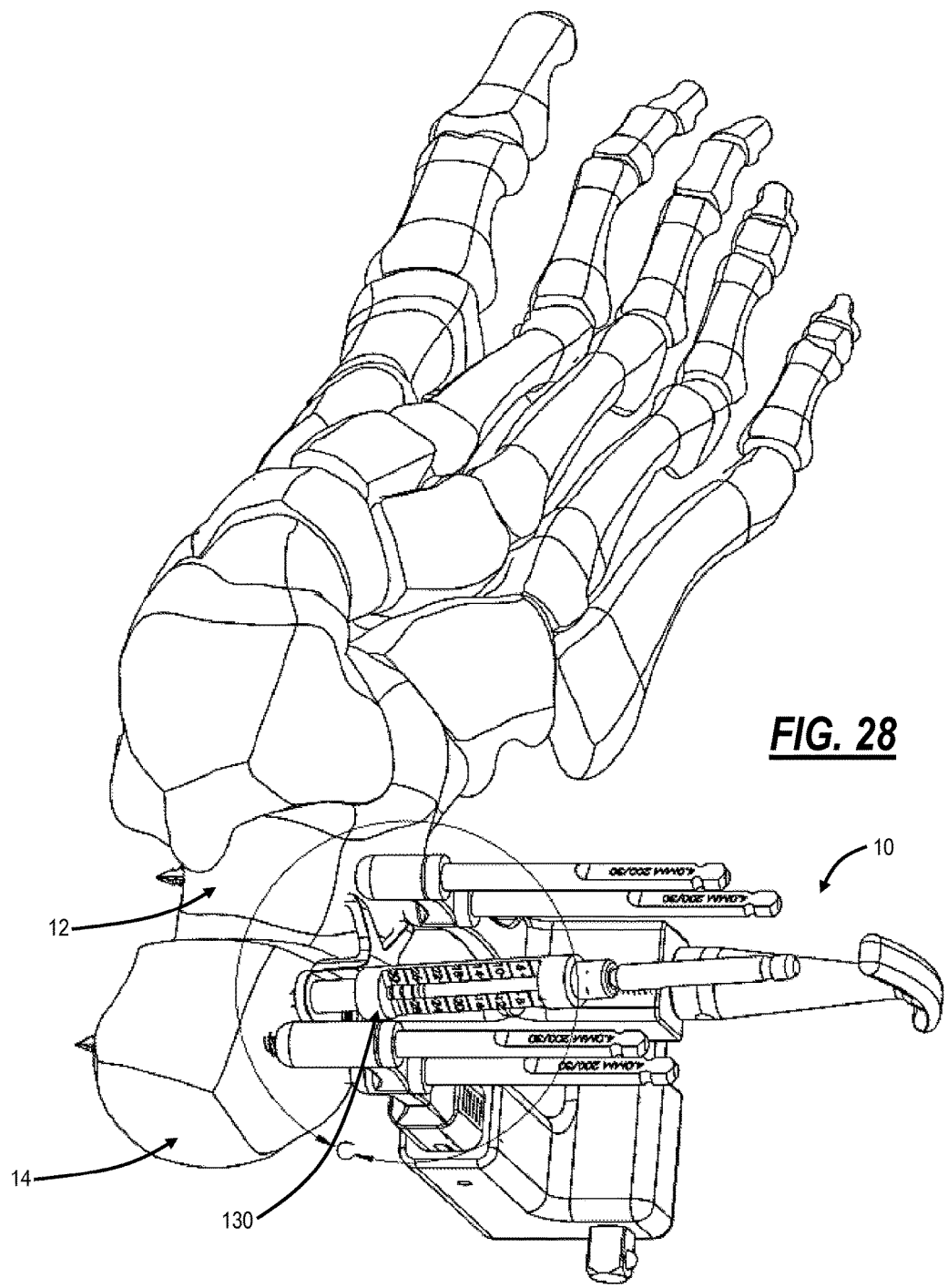
FIG. 28 is a perspective view of one exemplary embodiment of the surgical jig assembly implant device depth gauge of the present invention in use, coupled to the bony structures of the foot of a patient.

FIG. 28 is a perspective view of one exemplary embodiment of the surgical jig assembly implant device depth gauge 130 of the present invention in use, coupled to the bony structures 12 and 14 of the foot of a patient.

Figure 29:
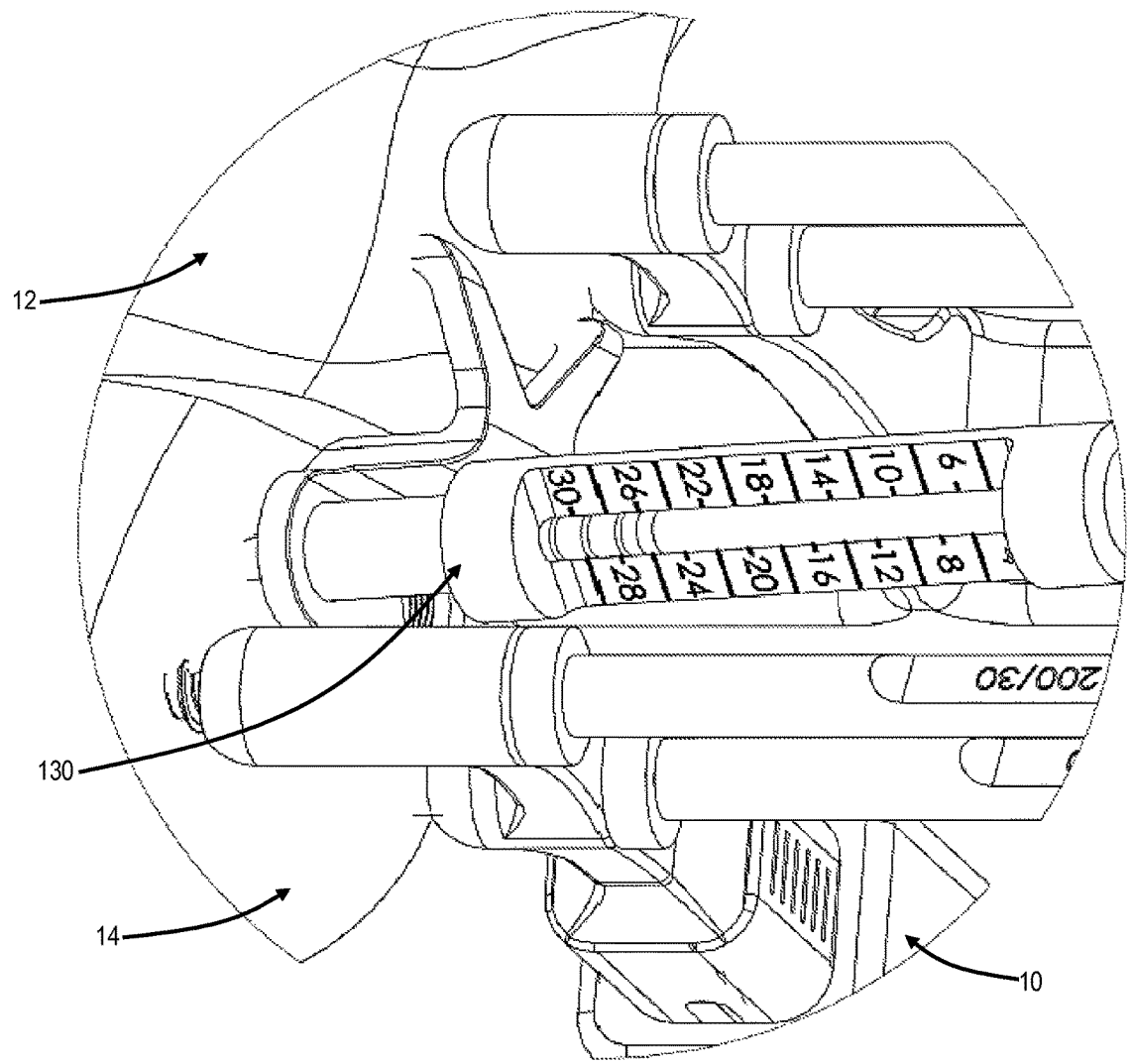
FIG. 29 is a partial perspective view of one exemplary embodiment of the surgical jig assembly implant device depth gauge of the present invention in use, coupled to the bony structures of the foot of a patient.

FIG. 29 is a partial perspective view further illustrating the surgical jig assembly implant device depth gauge 130 of the present invention in use, coupled to the bony structures 12 and 14 of the foot of a patient.

Figure 30:
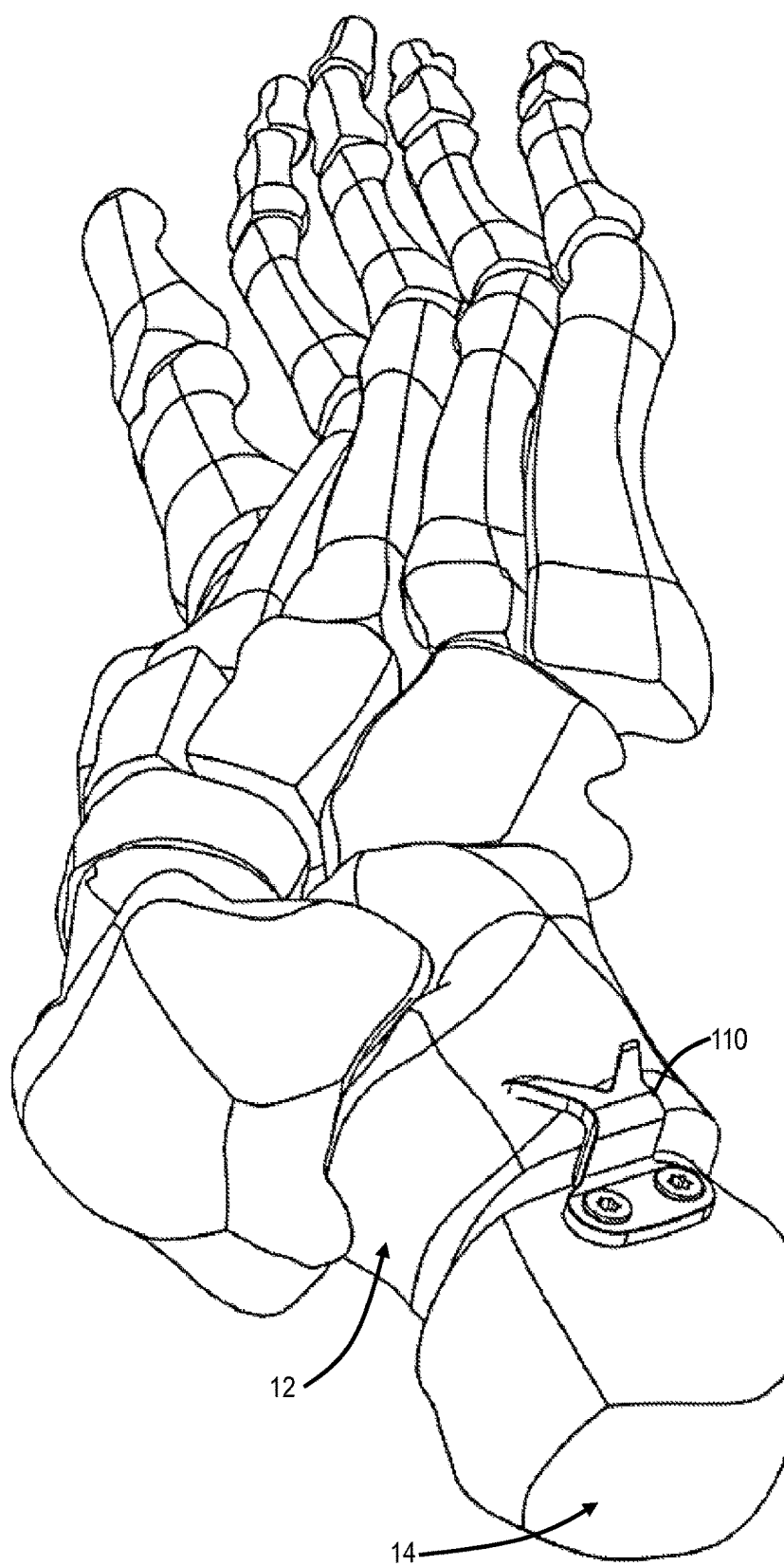
FIG. 30 is another perspective view of one exemplary embodiment of the surgical jig assembly implant device of the present invention in use, coupled to the bony structures of the foot of a patient.

FIG. 30 is another perspective view of one exemplary embodiment of the surgical jig assembly implant device 110 of the present invention in use, coupled to the bony structures 12 and 14 of the foot of a patient.

Although the present invention is illustrated and described herein with reference to preferred embodiments and specific examples thereof, it will be readily apparent to those of ordinary skill in the art that combinations of these embodiments and examples and other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical jig assembly that is configured to hold and manipulate a first bone segment and a second bone segment, comprising:
a first member that is configured to be selectively coupled to the first bone segment;
a second member threadedly coupled to the first member, wherein the second member selectively translates with respect to the first member along a first axis;
a third member threadedly coupled to the second member, wherein the third member selectively translates with respect to the second member along a second axis, wherein the second axis is perpendicular to the first axis; and
a fourth member threadedly coupled to the third member, wherein the fourth member selectively translates with respect to the third member along a third axis, wherein the third axis is perpendicular to both the first axis and the second axis, and wherein the fourth member is configured to be selectively coupled to the second bone segment.

2. The surgical jig assembly of claim 1, wherein the second member selectively rotates with respect to the first member about the first axis, the third member selectively rotates with respect to the second member about the second axis, and the fourth member selectively rotates with respect to the third member about the third axis.

3. The surgical jig assembly of claim 1, further comprising visual alignment guides disposed on a visible outer surface of any of the first member, the second member, the third member, and the fourth member.

4. The surgical jig assembly of claim 1, further comprising a drill guide for drilling holes in the first bone segment and the second bone segment corresponding to holes associated with the first member and the fourth member, thereby allowing the first member to be selectively coupled to the first bone segment and the fourth member to be selectively coupled to the second bone segment.

5. The surgical jig assembly of claim 1, further comprising a cut guide for cutting the first bone segment and the second bone segment, wherein the cut guide comprises holes corresponding to holes associated with the first member and the fourth member, and wherein the holes are configured to receive pins, thereby coupling the cut guide to and aligning the cut guide with the first member and the fourth member.

* * * * *